(12) United States Patent
Barkan et al.

(10) Patent No.: US 9,724,366 B2
(45) Date of Patent: Aug. 8, 2017

(54) CD11 B[LOW] MACROPHAGES AND CONDITIONED MEDIA THEREOF FOR TREATING CANCER AND/OR FIBROSIS

(71) Applicant: CARMEL-HAIFA UNIVRSITY ECONOMIC CORPORATION LTD., Haifa (IL)

(72) Inventors: Dalit Barkan, Zichron Yaakov (IL); Odelya Gilon, Kiryat Bialik (IL); Amiram Ariel, Kiryat Motzkin (IL); Sagie Schif-Zuck, Haifa (IL); Aroesti-Assi Simaan, Maale Adumim (IL)

(73) Assignee: Carmel-Haifa University Economic Corporation Ltd, Haifa (IL)

( * ) Notice: Subject to any disclaimer, the term of this patent is extended or adjusted under 35 U.S.C. 154(b) by 0 days.

(21) Appl. No.: 14/758,569

(22) PCT Filed: Dec. 30, 2013

(86) PCT No.: PCT/IL2013/051084
§ 371 (c)(1),
(2) Date: Jun. 30, 2015

(87) PCT Pub. No.: WO2014/102799
PCT Pub. Date: Jul. 3, 2014

(65) Prior Publication Data
US 2015/0342992 A1 Dec. 3, 2015

Related U.S. Application Data

(60) Provisional application No. 61/747,312, filed on Dec. 30, 2012.

(51) Int. Cl.
*A61K 35/15* (2015.01)
*A61K 45/06* (2006.01)
*C12N 5/077* (2010.01)
*C12N 5/0786* (2010.01)
*A61K 35/12* (2015.01)

(52) U.S. Cl.
CPC .............. *A61K 35/15* (2013.01); *A61K 35/12* (2013.01); *A61K 45/06* (2013.01); *C12N 5/0645* (2013.01); *C12N 5/0656* (2013.01); *C12N 2500/70* (2013.01); *C12N 2501/15* (2013.01); *C12N 2501/58* (2013.01); *C12N 2502/00* (2013.01); *C12N 2502/1157* (2013.01); *C12N 2506/11* (2013.01); *C12N 2506/115* (2013.01); *C12N 2506/1307* (2013.01)

(58) Field of Classification Search
CPC C12N 5/0645; C12N 5/0656; C12N 2501/58; C12N 2502/1157; C12N 2506/115; C12N 2506/11; C12N 2501/15; C12N 2502/00; C12N 2506/1307; A61K 35/12; A61K 35/15; A61K 45/06

USPC ................................ 424/93.71, 115; 435/366
See application file for complete search history.

(56) References Cited

U.S. PATENT DOCUMENTS 7,976,868 B2* 7/2011 Thorpe ................ A61K 39/395
424/450

OTHER PUBLICATIONS

Schiff-Zuck et al. Saturated-efferocytosis generates pro-resolving CD11blow macrophages: Modulation by resolvins and glucocorticoids. E. J. Immunol. (2011), v41, p. 366-379.*
G.J. Inman. Switching TGFb from a tumor suppressor to a tumor promoter. Curr Opin Genet Dev. (2011), v21(1), p. 93-99.*
Connolly et al. Complexities of Tgf-β Targeted Cancer Therapy. Int J Biol Sci. (2012), 8(7), p. 964-78.*
Solinas et al; "Tumor-conditioned macrophages secrete migration-stimulating factor: a new marker for M2-polarization, influencing tumor cell motility" Journal of immunology 185(1);pp. 642-652. (2010).
Barkan D et al: "Inhibition of metastatic outgrowth from single dormant tumor cells by targeting the cytoskeleton" Cancer Research , 68(15):pp. 6241-6250. (2008).
Barkan D, et al: "Metastatic growth from dormant cells induced by a col-I-enriched fibrotic environment." Cancer Research 70(14):pp. 5706-5716.(2010).
Barkan D et al: "An in vitro system to study tumor dormancy and the switch to metastatic growth". Journal of Visualized Experiments : JoVE 2011(54).
Barkan Dalit et al; "Extracellular Matrix: A Gatekeeper in the Transition from Dormancy to Metastatic Growth" Eur J Cancer. 46(7):pp. 1181-1188. (2010).
Barkan Dalit et al; "b1-Integrin: A Potential Therapeutic Target in the Battle against Cancer Recurrence" Clinical Cancer Research 17(23). pp. 7219-7223. (2011).
Satoshi Ueha et al; "Cellular and molecular mechanisms of chronic in flammation-associated organ fibrosis" frontiers in immunology vol. 3. pp. 1-6. (2012).
Eliver Eid Bou Ghosn et al; "CD11b expression distinguishes sequential stages of peritoneal B-1 development" PNAS, vol. 105 No. 13 pp. 5195-5200. (2008).
TA Wynn; "Cellular and molecular mechanisms of fibrosis" Journal of Pathology 214: pp. 199-210. (2008).
Ariel A, Serhan CN: "New Lives Given by Cell Death: Macrophage Differentiation Following Their Encounter with Apoptotic Leukocytes during the Resolution of Inflammation". Frontiers in Immunology 3:4. (2012).
Sagie Schif-Zuck et al; "Saturated-efferocytosis generates pro-resolving CD11blow macrophages: Modulation by resolvins and glucocorticoids" Eur. J. Immunol. 41: pp. 366-379. (2011).

* cited by examiner

*Primary Examiner* — Scott Long
*Assistant Examiner* — Sean C Barron
(74) *Attorney, Agent, or Firm* — Knobbe, Martens, Olson & Bear, LLP

(57) ABSTRACT

A conditioned medium of CD11b$^{low}$ macrophages and methods for preparing it are provided. Pharmaceutical compositions comprising the CD11b$^{low}$ macrophages conditioned medium or a culture of CD11b$^{low}$ macrophages and their use in the treatment of cancer or fibrosis are also provided.

4 Claims, 27 Drawing Sheets

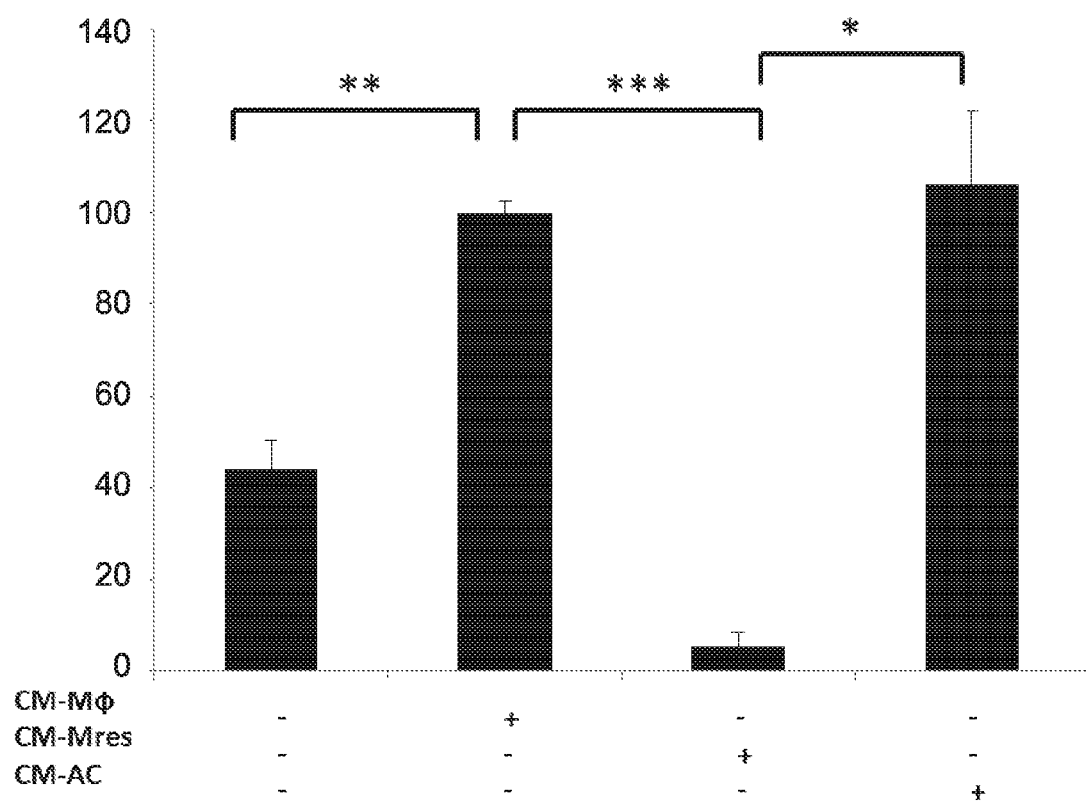

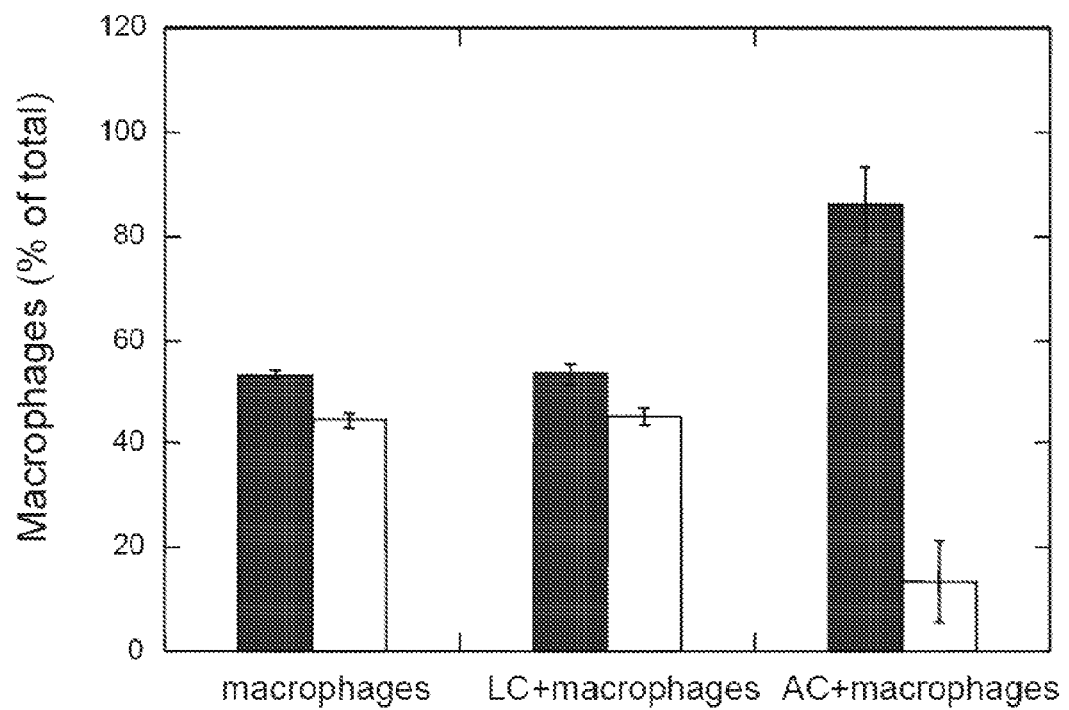

CD11 B[LOW] MACROPHAGES AND CONDITIONED MEDIA THEREOF FOR TREATING CANCER AND/OR FIBROSIS

TECHNICAL FIELD

The present invention relates, generally, to cell conditioned media and, more specifically, to cell conditioned media of specific types of macrophages and methods for preparation thereof. The invention further relates to compositions comprising said specific types of macrophages or a conditioned medium thereof and their uses in the treatment of cancer or fibrosis.

BACKGROUND ART

Metastasis and Tumor Dormancy

Early diagnosis of neoplastic disorders such as breast cancer, melanoma and renal cancer, can increase the chances of disease-free survival of patients. However, these disorders can recur as metastatic disease many years after primary tumor resection and adjuvant therapy. This metastatic disease appears to arise from tumor cells that disseminated early in the course of the disease but did not develop into clinically apparent lesions, and is the major cause of mortality of breast cancer patients.

These long-term surviving, disseminated tumor cells maintain a state of dormancy and are resistant to conventional therapies that target actively-dividing cells, but may be triggered to proliferate through largely unknown mechanisms. Therefore, understanding the mechanisms that regulate tumor dormancy or the switch to a proliferative state is critical to discovering novel targets and interventions to prevent disease recurrence.

Chemotherapy is the main treatment for disseminated, malignant cancers. However, chemotherapeutic agents are limited in their effectiveness for treating many cancer types, including many common solid tumors. This failure is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth.

In addition, currently available cancer therapy commonly targets actively proliferating tumor cells, and fails to eradicate quiescent, non-proliferating tumor cells (dormant tumor cells) which are the source for the recurrent disease and metastasis.

Two states of tumor dormancy have been described in the literature based on experimental and clinical evidence. Dormant tumor cells may exist in a quiescent state for many years as solitary quiescent tumor cells in the bone narrow, lymph nodes and blood circulation of breast cancer patients. Their quiescence was demonstrated by their negative staining for the proliferation marker Ki67 and their negative staining for apoptosis. These cells are resistant to conventional therapies that target actively dividing cells, leading to possible disease recurrence following adjuvant therapy.

Alternatively, tumor dormancy may exist as micrometastases where cellular proliferation is balanced by apoptosis. Consequently, in this balanced state, there is no net increase in tumor mass over time. These micrometastases remain dormant because of lack of recruitment of the vasculature needed to nourish the tumor, known as the angiogenic switch and/or involvement of the adaptive immune system such as cytotoxic CD8[+] T cells.

Macrophage Types

Macrophages are highly plastic monocyte-derived cells that acquire different molecular and functional phenotypes following exposure to different bioactive molecules and environments. The early studies on the interactions of macrophages and lymphocytes in battling bacterial infections revealed the T helper type 1 (Th1) secreted cytokine IFNγ to be involved in the classical activation of macrophages. However, seminal studies by the groups of Gordon and Mantovani have extensively characterized additional macrophage subtypes activated in alternative manners (reviewed in Mantovani et al., 2004, Martinez et al., 2009).

Since the major polarizing cytokines initially found to be involved in classical and alternative activation were derived from Th1 (IFNγ) and Th2 (IL-4 and IL-13) lymphocytes these activated macrophages were named M1 and M2, respectively. Later studies revealed that, in addition to IL-4, alternative activation can also be induced by immune complexes and glucocorticoids, and accordingly the subdivision of alternatively-activated macrophages to M2a-c was instilled. M1 macrophages are important inducers and effectors in the Th1 response. They are instrumental in immune responses against intracellular microbes and tumors. M2 macrophages are more heterogeneous, but generally play a role in Th2 responses, such as killing and encapsulation of extracellular parasites, stopping inflammation and promoting tissue repair and remodeling. M2 macrophages also play a role in immune regulation and promote tumor progression (Mantovani et al., 2005, Martinez et al., 2009). M1 and M2 macrophages are not only distinct in function, but also express different receptors and enzymes required for their activities. M1 macrophages express high levels of inflammatory cytokines (IL-12, IL-23, TNFα, IL-1β, and IL-6) and chemokines (CXCL9, 10, and 11, CCL2, 3, 4, and 5, and CXCL2), as well as enzymes involved in the generation of reactive oxygen species (ROS) and nitric oxide (NO). M2 macrophages express lower levels of inflammatory mediators, but high levels of IL-10, scavenger, mannose, and galactose receptors.

The prototypic Th2 cytokines IL-4, IL-13 and IL-10, as well as immune responses to parasites were found to promote many of the outcomes of efferocytosis (the process by which dying or dead cells are removed by phagocytic cells) in macrophages. These cytokines are well appreciated antagonists of the M1 response and macrophage pro-inflammatory properties while IL-4 and IL-13 can also promote fibrosis through TGFβ production. IL-4 and IL-13 also activate PPAR-λ and PPAR-δ to promote monocyte/macrophage alternative activation. Liver X receptor (LXR) was recently found to synergize with IL-4 in the induction of arginase 1 expression and promotion of an M2 phenotype in regressive atherosclerotic lesions. Thus, efferocytosis induces phenotypic and molecular switches and activates signaling pathways in macrophages that resemble M2 polarization. In addition, M2 polarization promotes efferocytosis through induction of different molecular modules, whereas M1 macrophages exert reduced uptake of apoptotic cells. Along these lines, recent studies also found that efferocytosis is a self-promoting process, and that M2 pathways play key roles in mediating this feature of macrophage function.

Role of Macrophages in Inflammation

When inflammation occurs, polymorphonuclear neutrophils (PMNs) are among the first leukocyte responders to accumulate in the inflamed site. These cells are crucial as the first line of defense of the innate immune system because of their phagocytotic and microbicidal functions. The initial accumulation of neutrophils is followed by a second wave of cellular infiltration, of mononuclear phagocytes (monocytes). Differentiation of monocytes into macrophages promotes the removal of apoptotic neutrophils and debris by nonphlogistic phagocytosis. Notably, the apoptotic neutrophil uptake blocks the release of pro-inflammatory mediators (including chemokines, cytokines and lipid mediators) from M1 macrophages, in a phenomenon termed reprogramming/"immune silencing", and promotes production and release of anti-inflammatory and reparative cytokines (M2 macrophages). These M2 macrophages promote myofibroblast proliferation, support matrix deposition, and express inhibitors of metalloproteinase that impairs the remodeling of deposited ECM (Ariel et al., 2012). Therefore, the milieu that governs macrophage differentiation along the M1-M2 axis may dictate the magnitude of myofibroblast activation and deposition of ECM.

Extra Cellular Matrix (ECM) as a Regulator of Tumor Dormancy

In recent studies, the inventors have clarified potential mechanisms by which the ECM, which is part of the microenvironment milieu surrounding the dormant tumor cells, may regulate tumor dormancy and its outbreak to growing metastases (Barkan et al., 2008, 2010 and 2010a). Specifically, it was shown that ECM composition may play a critical role in determining whether solitary dormant tumor cells remain quiescent or begin to actively proliferate, using the well-characterized D2.0R/D2A1 mammary cell line model system to study dormant vs. metastatic proliferative growth. These cell lines were derived from tumors arising from implants of the same D2 hyperplastic alveolar nodule line, but display distinct metastatic properties. Whereas disseminated D2A1 cells in mice transition from dormancy to metastatic growth after few weeks, disseminated D2.0R cells remain dormant for months with occasional formation of metastatic lesions. Using a modified 3D culture system constituted from growth factor reduced basement membrane (BME; a specialized form of ECM), the inventors demonstrated for the first time that the quiescent or proliferative behavior of these cells could be recapitulated in vitro (Barkan et al., 2010a; Barkan et al., 2011). Thus D2.0R cells persist in a quiescent state for at least 14 days in the 3D BME system and only few cells occasionally emerge from dormancy after this period. D2A1 cells, on the other hand, remain quiescent for only 4-6 days in the 3D BME system and then begin to proliferate extensively. Importantly, the quiescent state is characterized by growth arrest associated with expression of the negative cell-cycle regulators p27 and p16, and is not due to a balance between cell proliferation and apoptosis. Notably, this 3D model system was validated with additional cell lines demonstrating dormant and metastatic behavior in vivo. Hence, the model system provides the first in vitro method to model tumor dormancy and study the transition to proliferative growth induced by the microenvironment.

Characterization of Fibrotic Tissue

Fibrosis is one of the pathological features of metastatic outbreak and is a major pathological feature of many other diseases. Fibrosis can lead to permanent scaring, organ malfunction and, ultimately, death, as seen in end-stage liver disease, kidney disease, idiopathic pulmonary fibrosis and heart failure. There are some drugs aimed to treat fibrotic disease, such as corticosteroids (to decrease Col-I synthesis) and angiotensin blocking agents (for inhibition of collagen synthesis and TGFβ1). Unfortunately, none of them has the ability to cure fibrosis.

Excessive deposition of matrix proteins such as Col-I and fibronectin and α-smooth muscle actin (α-SMA) expression in differentiated fibroblasts are the hallmarks of fibrotic processes. Fibrosis is a complex and tightly orchestrated phenomenon; it involves multiple signals mediated by various stromal cells, such as myofibroblasts (which differentiate from fibroblasts), endothelial cells and macrophages.

Fibroblasts are considered to be the primary source of the reparative matrix in all tissues. In response to tissue injury, they proliferate, migrate to the site of injury, and differentiate into their activated form, myofibroblasts. Following differentiation, myofibroblasts acquire an increased contractile ability and are characterized by the expression of α-SMA positive phenotype. In wound healing, these myofibroblasts mediate wound contraction and the formation of a collagen-rich extracellular matrix. Increased activation and proliferation of resident fibroblasts at the wound edge is therefore an important early step that is central to the wound healing process.

The cytokine transforming growth factor-β1 (TGFβ1) is a mediator of tissue repair and wound healing and is also implicated in progressive tissue fibrosis. In addition to its effect on extracellular matrix turnover, TGFβ1 is known to have direct effects on cell phenotype, including the induction of a contractile phenotype and the up-regulation of α-SMA both in vitro and in vivo.

The myofibroblast, by virtue of its ability to express high levels of cytokines, extracellular matrix and α-SMA, is expected to have key roles in inflammation, connective tissue deposition, and lung tissue mechanics, respectively, but that can severely impair organ function when contraction and ECM protein secretion become excessive, such as in fibrosis.

Fibrosis occurs upon deregulated and exaggerated tissue repair that fails to subside and resolve. During active resolution of inflammation, specific signals down-regulate macrophage activation and promote the clearance of activated macrophages, either by apoptosis or by migration through the lymphatic drainage. Disruption of any of these processes can lead to chronic persistent inflammation and fibrosis.

Fibrotic-Like Microenvironment Promotes Dormant Tumor Cells Proliferation

A recent report by Barkan and colleagues has demonstrated for the first time that remodeling of the ECM can regulate the switch of dormant tumor cells to their metastatic outgrowth. Specifically, it has been shown that metastatic D2A1 cell line transitioned from a quiescent state to proliferation upon production of fibronectin in vitro (Barkan et al., 2008). Furthermore, metastatic lesions arising from D2A1 cells in vivo were associated with significant deposition of fibronectin and type I Collagen (Col-I), whereas a related dormant D2.0R cell line did not express fibronectin or Col-I. However, supplementing the 3D BME system with fibronectin and or Col-I induced the transition of D2.0R cells from quiescence to growth. Furthermore, it has been recently demonstrated by the inventors for the first time that the induction of fibrosis, with deposition of Col-I in the in vivo metastatic microenvironment, induced dormant D2.0R cells to form proliferative metastatic lesions (Barkan et al., 2010a). Hence, D2A1 cells were able to escape tumor dormancy by inducing a stromal fibrotic-like response in vivo, whereas D2.0R cells required an exogenous fibrotic stimulus to initiate their proliferative response.

Importantly, these findings are consistent with several clinical observations demonstrating a correlation between fibrosis and breast cancer recurrence (Hasebe et al., 2002). Therefore, a fibrotic-like microenvironment, which can either be induced externally or be associated with the pathology induced by the residing tumor cells, may provide the permissive microenvironment triggering the transition from dormancy to metastatic growth.

Immunomodulating therapies designed to affect various immune cells which may positively or negatively affect tumor progression are also being considered as potential modulators in the treatment of cancer and other pathologies.

WO 1999/029345 discloses a method for the inhibition of angiogenesis in a cell population in a mammal by inhibiting a host cell angiogenic effect in said mammal, optionally by creating for said cell population an environment substantially free of activated macrophages. The method is said to be useful for the treatment of cancer. Other publications based on inhibiting or eliminating macrophages are disclosed in US 2009/258025 and WO 2010/091206.

EP 0211684 discloses a method of promoting tumoricidal activity of cells of macrophage lineage, comprising the step of subjecting the cells of macrophage lineage to an effective amount of a granulocyte-macrophage colony stimulating factor.

US 2003/0108534 discloses a method of treating cancer, comprising administering to a patient in need an effective amount of macrophages produced by culturing monocytes in vitro, said macrophages having at least one of the following properties: their cytotoxic activity without IFN-γ is increased with respect to standard macrophages; their cytotoxic activity is increased with IFN-γ with respect to standard macrophages; and deactivation of the cytotoxic activity following activation of IFN-γ is defined by residual cytotoxic activity compared to the maximum cytotoxic activity presented by the macrophages due to IFN-γ activation.

Macrophages have also been reported to be involved in anti-cancer effects induced by *Mycobacterium bovis* bacillus Calmette-Guérin immunotherapy of bladder cancer (Luo and Knudson, 2010).

Thus, a number of distinct macrophages phenotypes may exist in the mammalian body during different stages of inflammation and pathology and during steady state homeostasis. Different macrophage populations have been suggested to exert opposing effects on tumor progression and inflammation. In addition, interactions between the macrophages and their environment, such as the inflammatory site, may also influence the phenotype and hence the function of the macrophages. It is therefore considered difficult to determine appropriate parameters for using macrophages for controlled, predictable therapy, and indeed their clinical use is currently limited.

None of the prior art discloses or fairly suggests that isolated macrophage populations may be used for preventing the recurrence of cancer and metastatic progression in patients having cancer remission. There remains an unmet medical need for providing effective and safe treatments for the treatment of cancer, and especially for treating patients in cancer remission against tumor recurrence. Identification of isolated macrophages and secretory products thereof for inducing cell death in dormant, non-proliferating cells would be highly advantageous.

SUMMARY OF INVENTION

It has now been unexpectedly found in accordance with the present invention that certain types of macrophages, particularly macrophages, herein designated $CD11b^{low}$ macrophages, characterized by CD11b expression that is significantly lower than surface expression of this marker on activated inflammatory macrophages, or a conditioned medium of said $CD11b^{low}$ macrophages, can be useful for inducing cell death in malignant cells, including dormant, non-proliferating tumor cells. These cells and the conditioned medium thereof were also unexpectedly found to inhibit fibrosis as manifested by inhibition of the transition of fibroblasts into myofibroblasts, including inhibition of Type I collagen (Col-I) secretion and of α-SMA expression.

Thus, in one aspect, the invention is directed to a conditioned cell culture medium of $CD11b^{low}$ macrophages or a biologically active fraction thereof. In preferred embodiments, said conditioned medium is of $CD11b^{low}$ human macrophages.

In another aspect, the invention is directed to a method for preparing said conditioned cell culture medium of $CD11b^{low}$ macrophages, the method comprising:

(i) culturing a population of mononuclear cells of the monocyte/macrophage lineage for 5-7 days, so as to induce differentiation of said mononuclear cells to macrophages;

(ii) incubating the macrophages obtained in (i) with apoptotic cells or in the presence of a pro-resolving lipid mediator to reduce the CD11b expression, thus obtaining a culture of $CD11b^{low}$ macrophages; and (iii) collecting the conditioned cell culture medium of $CD11b^{low}$ macrophages.

In some embodiments, the mononuclear cells of the monocyte/macrophage lineage used in the method above are monocytes. In some embodiments, the monocytes are human monocytes. In preferred embodiments, the monocytes are autologous, namely, they are obtained from the patient to whom the $CD11b^{low}$ macrophages or a conditioned medium thereof will be administered.

In some embodiments, the mononuclear cells of the monocyte/macrophage lineage are human monocytes isolated from a blood sample of an individual by any conventional method followed by suspending the cells in a suitable medium. In some embodiments, the human monocytes are derived from peripheral blood mononuclear cells (PBMC) of an individual, preferably autologous PBMC.

In some embodiments, the human monocytes are cultured in step (i) in autologous serum or in a suitable medium to which granulocyte-macrophage colony stimulating factor (GM-CSF) or macrophage colony stimulating factor (M-CSF) is added, and are then differentiated into a population of human macrophages.

In some embodiments, for reduction of the CD11b marker expression, the macrophages obtained in step (ii) are incubated in the presence of apoptotic cells. In some preferred embodiments, the ratio of said macrophages to the apoptotic cells is between 1:1 and 1:1.5.

In some other embodiments, for reduction of the CD11b marker expression, the incubation of the macrophages in step (ii) is carried out in the presence of a pro-resolving lipid mediator, which may be selected from a lipoxin (LX) such as $LXB_4$ or 15-epi-$LXA_4$, a resolvin (Rv) such as RvD1 or RvD2, a protectin (PD) such as protectin PD1, a maresin (MaR), or a glucorticoid such as dexamethasone.

In some embodiments, the invention is further directed to a conditioned cell culture medium of $CD11b^{low}$ human macrophages produced according to the method of the invention described hereinabove.

In a further aspect, the present invention relates to a pharmaceutical composition comprising the conditioned cell culture medium of $CD11b^{low}$ macrophages of the invention, or a biologically active fraction thereof, and a pharmaceutically active carrier, excipient or diluent.

In some embodiments, the invention relates to the conditioned cell culture medium of $CD11b^{low}$ macrophages, a biologically active fraction thereof or the pharmaceutical composition comprising said conditioned medium or said active fraction, for use in the treatment of cancer or fibrosis.

When the invention is directed to treatment of cancer, said treatment may comprise preventing or delaying cancer recurrence or occurrence of metastasis. In some embodiments, said treatment of cancer comprises inhibiting cancer metastasis. The cancer may be selected from breast, prostate, esophageal, skin, lung, head and neck, colon or liver cancer. In some embodiments, the cancer is breast cancer.

When the invention is directed to treatment of fibrosis, said treatment may comprise preventing or inhibiting fibrosis. In some embodiments, the fibrosis is associated with cancer. In some other embodiments, the fibrosis is associated with a disease or a condition selected from acute lung injury, Alzheimer's disease, chronic diabetic wounds, chronic granulomatous disease (CGD), chronic obstructive pulmonary disease (COPD), constrictive pericarditis, Dupuytren's disease, emphysema, hypertrophic burn scars, keloid, liver cirrhosis, plantar fibromatosis, retinal detachment inflammation, scleroderma, cystic fibrosis, endometrial fibrosis, idiopathic pulmonary fibrosis, myocardial fibrosis, nephrogenic fibrosis, pancreatic fibrosis, perineural fibrosis, renal interstitial fibrosis, secondary fibrosis in the gastrointestinal tract or fibrosis resulting after surgery.

In a further aspect, the present invention is directed to a culture of isolated $CD11b^{low}$ human macrophages or a a pharmaceutical composition comprising said culture and a pharmaceutically active carrier, excipient or diluent, for use in the treatment of cancer or fibrosis.

According to this aspect of the invention, a method is provided for preparing a culture of said human $CD11b^{low}$ macrophages, the method comprising:

(i) culturing a population of human mononuclear cells of the monocyte/macrophage lineage for 5-7 days, so as to induce differentiation of said mononuclear cells to macrophages; and (ii) incubating the macrophages obtained in (i) with apoptotic cells or in the presence of a pro-resolving lipid mediator to reduce the CD11b expression, thus obtaining a culture of $CD11b^{low}$ human macrophages.

All the features described above for the preparation and uses of the conditioned medium of $CD11b^{low}$ human macrophages apply mutatis mutandis to the preparation and uses of the culture of human $CD11b^{low}$ macrophages and the pharmaceutical composition comprising said culture.

In yet a further aspect, the present invention provides a method for treating cancer comprising administering to a subject in need an effective amount of an active agent selected from: (i) a conditioned cell culture medium of $CD11b^{low}$ macrophages; (ii) a biologically active fraction thereof; (iii) a pharmaceutical composition comprising (i) or (ii) and a pharmaceutically active carrier, excipient or diluent; (iv) a culture of human $CD11b^{low}$ macrophages; or (v) a pharmaceutical composition comprising (iv) and a pharmaceutically active carrier, excipient or diluent, wherein said treatment comprises preventing or delaying cancer recurrence or occurrence of metastasis or inhibiting cancer metastasis.

In some embodiments, the above method of preventing or delaying cancer recurrence or occurrence of metastasis, or inhibiting cancer metastasis, comprises preventing or inhibiting an outbreak of dormant cancer cells, particularly wherein said subject in need is in cancer remission.

In still a further aspect, the present invention provides a method for treating fibrosis comprising administering to a subject in need an effective amount of an active agent selected from: (i) a conditioned cell culture medium of $CD11b^{low}$ macrophages; (ii) a biologically active fraction thereof; (iii) a pharmaceutical composition comprising (i) or (ii) and a pharmaceutically active carrier, excipient or diluent; (iv) a culture of human $CD11b^{low}$ macrophages; or (v) a pharmaceutical composition comprising (iv) and a pharmaceutically active carrier, excipient or diluent, wherein said treatment comprises preventing or inhibiting fibrosis.

In some embodiments, the above method of preventing or inhibiting an outbreak of dormant cancer cells is achieved by preventing or treating fibrosis associated with said dormant cancer cells.

In some embodiments, the method for treating cancer may be performed in combination with one or more anti-cancer agents or treatments.

BRIEF DESCRIPTION OF THE DRAWINGS

In FIGS. 3C-G, black bars: LPS, white bars: vehicle (RPMI 10% FBS). Significant differences by Student's t test between $CD11b^{high}$ and $CD11b^{low}$ macrophages or between vehicle and LPS-stimulated macrophages (* P value<0.05,  P value<0.005, * P value<0.001) are indicated.

FIG. 16 shows abolishment of Col-I expression in MEF cells cultured in 3D BME culture upon CM-Mres treatment. Quantification of Col-I expression by MEF cultured in the 3D BME system is shown in the following treatments, from left to right: untreated, treated with CM-Mφ, CM-Mres or CM-AC. Values were normalized to CM-Mφ treatment (n=3; *: p≤0.05; : p≤0.01; *: p≤0.001).

FIGS. 17A-17C show that conditioned media of pro-resolving CD11b$^{low}$ macrophages induces apoptosis of outbreaking (day 4) dormant D2A1 cells in the 3D BME system. A. Generation and characterization of macrophage populations enriched for CD11b$^{high}$ (white bars) or CD11b$^{low}$ (black bars) macrophages. From left to right: macrophages only; with addition of live Jurkat cells (LC); with addition of apoptotic Jurkat cells (AC). B. Proliferation of D2A1 cells in the 3D system overlaid on day 4 (prior to their transition from dormancy to proliferation) with conditioned media from the different macrophage populations (from left to right): untreated, treated with apoptotic Jurkat cells (AC); treated with CD11b$^{high}$ macrophages; treated with CD11b$^{high}$ macrophages and live Jurkat cells (LC); treated with CD11b$^{low}$ macrophages. *: P≤0.001. C. Proliferation (normalized to control) of D2A1 cells in the 3D system overlaid on day 2 (when dormant) with conditioned media from the different macrophage populations (from left to right): untreated macrophages; enriched with CD11b$^{high}$ macrophages; enriched with CD11b$^{low}$ macrophages; ( P value<0.005, *** P value<0.001).

DETAILED DESCRIPTION OF THE INVENTION

Recently, some of the inventors of the present application identified and characterized a novel subset of pro-resolving macrophages designated CD11b$^{low}$ macrophages that appear during the resolution of murine peritonitis (Schif-Zuck et al., 2011). Furthermore, they found that these macrophages display an enzyme expression signature distinct from either M1 or M2 macrophages. CD11b$^{low}$ macrophages can be generated in vivo or ex vivo from M2-like macrophages that are characterized by high levels of CD11b expression and termed CD11b$^{high}$ macrophages, following the engulfment of apoptotic leukocytes, which is a hallmark of resolution. Furthermore, these newly discovered pro-resolving CD11b$^{low}$ macrophages, also termed resolution-promoting macrophages or Mres, lost their phagocytic potential and were prone to migrate to lymphoid tissues.

In the present invention, the inventors show for the first time that conditioned media of these recently described CD11b$^{low}$ macrophages can inhibit fibrosis, as manifested by inhibition of the transition of fibroblasts into myofibroblasts, including inhibiting Type I collagen (Col-I) secretion and α-SMA expression. The inventors have further surprisingly found that a conditioned medium of CD11b$^{low}$ macrophages has highly effective cytotoxic and cytostatic activities. Specifically, using a three-dimensional culture system that models tumor dormancy and outbreak of disseminated tumor cells it was unexpectedly found that the conditioned medium not only inhibited the proliferation of outbreaking dormant tumor cells, but also eradicated effectively even non-proliferating dormant tumor cells, which are largely resistant to currently used chemotherapeutic agents. These characteristics indicate that the conditioned medium may be useful for preventing or inhibiting metastasis and preventing the recurrence of cancer after remission.

Figure 9A:
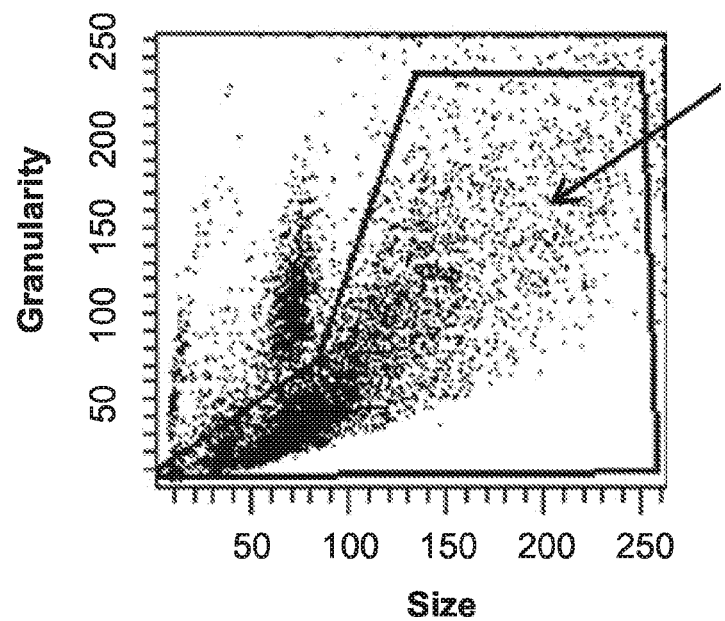
FIGS. 9A-9E show the generation of CD11b$^{high}$ enriched macrophages for ex vivo experiments. A. Selection of macrophages from exudates based on their size and granularity, arrow points to the relevant area of size and granularity. B. Histogram of identified macrophages, stained positively for F4/80. C. Percentage of macrophages (Mφ) (identified by positive staining for F4/80) and other cells (negative staining for F4/80 in peritoneal exudates), (n=5, *: p≤0.05). D. Characterization of macrophages stained positively for F4/80 by CD11b expression levels. CD11b$^{high}$ and CD11b$^{low}$ are shown. E. Percentage of CD11b$^{high}$ and CD11b$^{low}$ macrophages before incubation with apoptotic cells (AC) (n=3, **: p≤0.01).
Figure 9B:
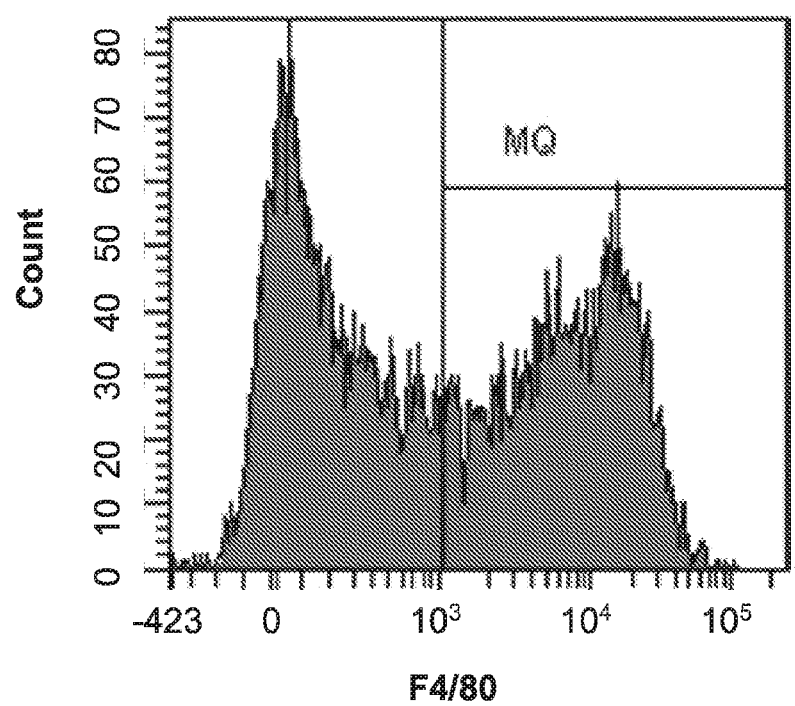
Figure 9C:
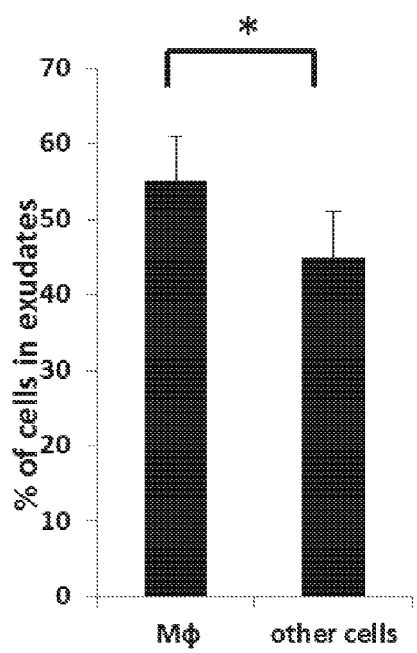
Figure 9D:
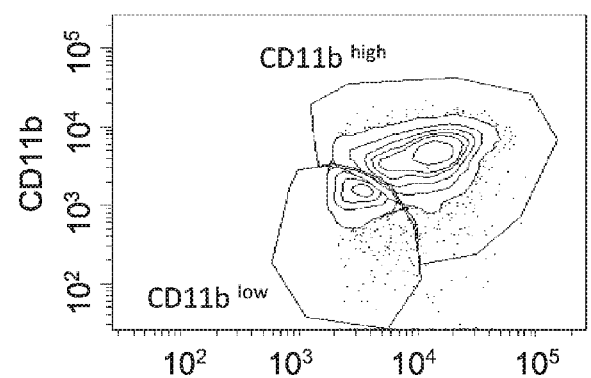
Figure 9E:
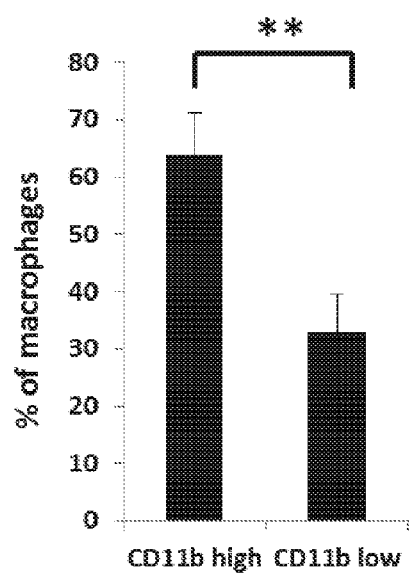

CD11b$^{high}$ and CD11b$^{low}$ macrophages are two populations of macrophages typically isolated in murine models from peritoneal exudates during the resolution phase of peritonitis. As can be seen in FIGS. 9D and 9E, fluorescence activated cell sorter (FACS) analysis shows the two populations: the majority of cells expressing high levels of CD11b (CD11b$^{high}$) and the minority of cells expressing low levels of CD11b (CD11b$^{low}$). The whole population of macrophages isolated from the resolution phase of inflammation is termed hereinbelow as "resolution-phase macrophages".

The level of CD11b or other markers may be determined by various methods known in the art, e.g. immunostaining and FACS analysis, or gel electrophoresis and Western blotting. The term "CD11b$^{high}$ macrophages", as used herein, relates to macrophages expressing high levels of CD11b. The term "CD11b$^{low}$ macrophages", as used herein, relates to macrophages that express on their surface a level of CD11b that is substantially lower than that of Cd11b$^{high}$ macrophages. Sometimes the term "CD11b deficient macrophages" is used to define "CD11b$^{low}$ macrophages" and both terms should be considered as synonyms.

The term "culture macrophages" refers herein to human macrophages differentiated in culture from peripheral blood mononuclear cells (PBMC). Culture macrophages are typically obtained by incubating PBMC for 5-7 days. In some embodiments, the cells are cultured in the presence of autologous serum (e.g. 1-10%, preferably 10%), this being serum obtained from the blood of the patient to whom the culture of CD11b$^{low}$ macrophages or the conditioned medium thereof will be administered. In some other embodiments, the cells are cultured in a suitable medium such as RPMI 1640, supplemented with 10% human serum, 2 mM L-glutamine, 100 μg/ml streptomycin, and 100 units/ml penicillin, to which granulocyte-macrophage colony stimulating factor (GM-CSF; e.g. 10 μg/ml) or, preferably, macrophage colony stimulating factor (M-CSF; e.g. 25 μg/ml), has been added.

It is shown herein that expression of CD11b on Cd11b$^{high}$ macrophages was about tenfold higher than its expression on CD11b$^{low}$ macrophages. The amount of CD11b in protein extracts of CD11b$^{low}$ macrophages was also significantly lower than its amount in the extracts from CD11b$^{high}$ macrophages (see Example 1).

Thus, according to some embodiments of the invention, the mean level of expression of CD11b$^{low}$ macrophages is defined as being 2-100 times lower than the mean CD11b expression on CD11b$^{high}$ macrophages or on culture macrophages. According to some embodiments, the mean level of expression of CD11b$^{low}$ macrophages is 2-10 times lower than the mean CD11b expression on CD11b$^{high}$ macrophages or on culture macrophages. According to some embodiments, the mean level of expression of CD11b$^{low}$ macrophages is 11-100 times lower than the mean CD11b expression on CD11b$^{high}$ macrophages or on culture macrophages. According to some embodiments, the level of CD11b expression on CD11b$^{low}$ macrophages is undetectable. Thus, according to some embodiments, the level of CD11b expression on CD11b$^{low}$ macrophages may be defined as 0 (zero). All the CD11b level measurements define surface expression detected by flow cytometry.

As mentioned above and explained in more detail below, CD11b$^{low}$ murine macrophages can be isolated from a macrophage population retrieved during the resolution phase of murine peritonitis. Additionally, CD11b expression on the surface of both CD11b$^{high}$ and CD11b$^{low}$ macrophages can be significantly reduced following their incubation with apoptotic cells (see Examples 6, 9). However, following incubation with apoptotic cells, some of the macrophages have even lower expression levels of CD11b compared to the level of expression found for CD11b$^{low}$ macrophages isolated from peritoneal exudates, and are termed CD11b$^-$ macrophages. Therefore the ex vivo-generated population of macrophages expressing low levels of CD11b may be comprised from both CD11b$^{low}$ and CD11b$^-$ macrophages.

Accordingly, the definition of CD11b$^{low}$ macrophages also includes CD11b$^-$ macrophages that are substantially devoid of surface CD11b or have very low, barely detectable, levels of CD11b or no CD11b at all.

According to some embodiments of the present invention, the population of CD11b$^{low}$ macrophages is comprised of a heterogeneous population of cells. Typically, at least 50% of the heterogeneous populations of cells are CD11b$^{low}$ macrophages. In some embodiments, more than 55%, 60%, 65%, 70%, 75% or more than 80% of the cells are CD11b$^{low}$ macrophages in heterogeneous populations [see FIGS. 10, 11].

In some embodiments, the population of CD11b$^{low}$ macrophages is comprised of a homogeneous population, meaning that it is substantially devoid of macrophages that are not CD11b$^{low}$ macrophages.

The terms "CD11b deficient macrophages", "resolution-promoting macrophages", "pro-resolving macrophages", or "Mres" are used hereinbelow interchangeably with, and have the same meaning as, "CD11b$^{low}$ macrophages".

The effect of treating mouse embryonic fibroblasts (MEF) with a conditioned medium from CD11b$^{low}$ macrophages was shown in Examples 10-14. To mimic the process of fibrosis, mouse embryonic fibroblasts (MEFs) were induced to differentiate to myofibroblasts by treating the cells with TGFβ1. As shown in Example 10, treatment with conditioned medium from Mres (CD11b$^{low}$ macrophages) of MEFs which were induced with TGFβ, resulted in less proliferation than treatment with conditioned medium from CD11b$^{high}$ macrophages. Further, according to Example 11, this lack of proliferation was most likely due to growth arrest, since most of the MEFs were alive and did not stain by a TUNEL assay, which detects apoptosis. Example 12 shows that conditioned medium from CD11b$^{low}$ significantly inhibited the expression of α-SMA in MEF (α-SMA marks their differentiation to myofibroblasts) treated with TGFβ1 compared to the expression levels in MEF treated with TGFβ1+conditioned medium from CD11b$^{high}$ macrophages. According to Examples 13 and 14, conditioned medium from CD11b$^{low}$ macrophages significantly inhibited Col-I expression of TGFβ1-treated MEFs compared to untreated MEFs and to TGFβ1-treated MEFs that were treated with conditioned medium from CD11b$^{high}$ macrophages.

Additionally, the effect of a conditioned medium from CD11b$^{high}$ macrophages on the proliferation of dormant tumor cells was shown in Examples 15 and 16 for tumor cells cultured in a modified 3D culture system constituted from growth factor reduced basement membrane (BME; a specialized ECM). This 3D BME system, described recently in Barkan et al., 2011, can model tumor dormancy and outgrowth. Supplementing the 3D BME system with Col-I was shown to induce the transition of dormant tumor cells from quiescence to proliferative growth. Example 15 shows that conditioned media from CD11b$^{high}$ cells induced cell death in outbreaking tumor cells during their transition from dormancy to proliferation in the 3D system, and also of dormant tumor cells. Additionally, Example 16 shows that treating dormant tumor cells co-cultured in the 3D BME system with a conditioned medium from CD11b$^{high}$ macrophages causes them to emerge from their dormant state, but treatment with a conditioned medium from CD11b$^{low}$ macrophages prevented Col-I expression by the differentiated MEFs and resulted in lower numbers of tumor cells.

In one aspect of the invention, there is provided a conditioned cell culture medium of CD11b$^{low}$ macrophages or a biologically active fraction thereof.

The term "conditioned medium" in general refers to a growth medium in which cells have been cultured/incubated for a period of time followed by harvest of such medium from the cultured cells. A conditioned medium contains metabolites, growth factors, and extracellular matrix proteins secreted into the medium by the cultured cells.

In accordance with the present invention, the term "conditioned medium of CD11b$^{low}$ macrophages" refers to the medium harvested from the cultured macrophages after the incubation with either apoptotic cells or with a pro-resolving lipid mediator, when the CD11b$^{low}$ macrophages are obtained. The conditioned medium may be derived from autologous serum or from a medium suitable for culture of monocytes such as, but not limited to, Iscove's Modified Dulbecco's Medium (IMDM) and RPMI 1640, and may contain additional nutrients.

In some embodiments of the invention, the conditioned medium of CD11b$^{low}$ macrophages is based on RPMI 1640 with 10% fetal bovine serum (FBS) or 10% human serum and supplemented with 2 mM L-glutamine, 100 µg/ml streptomycin, and 100 units/ml penicillin. It also contains soluble factors secreted by the cultured cells into the medium. The conditioned medium may be purified, e.g. by filtration or centrifugation, to provide substantially cell free preparations.

In the method for preparing the conditioned medium of the invention, in a first step a population of mononuclear cells of the monocyte/macrophage lineage, preferably human monocytes, is cultured for 5-7 days, so as to induce differentiation of said mononuclear cells/monocytes to macrophages. The culture is made in autologous serum or in a medium suitable for culture of monocytes as defined above in paragraphs [0071] and [0083].

In a second step of the method, the macrophages obtained in the first step, which are mainly CD11b$^{high}$ macrophages, are incubated with an agent that will reduce the CD11b expression of the macrophages so as to obtain a macrophage population mainly constituted of CD11b$^{low}$ macrophages.

In some embodiments, the agent used for reduction of the CD11b expression of macrophages is apoptotic cells.

As shown in Example 1 hereinafter, CD11b$^{high}$ and the CD11b$^{low}$ macrophage populations are distinct populations, as shown by the difference in protein expression profiles between these two populations, For example, CD11b$^{low}$ macrophages may express lower levels (typically 2-10 times lower) of COX-2 and/or MMP-9 compared to CD11b$^{high}$ macrophages. CD11b$^{low}$ macrophages may also express 12/15-LO at a level significantly higher than CD11b$^{high}$ macrophages. CD11b$^{low}$ typically express iNOS, arginase-1 or actin a significantly reduced level compared to CD11b$^{high}$ macrophages, or in the case of iNOS or arginase-1, possibly not at all.

CD11b$^{low}$ macrophages may therefore be further characterized by their expression level of certain additional markers, such as an increased expression level of 12/15-LO and/or a reduced expression level of iNOS, arginase-1 or actin.

Example 2 shows that CD11b$^{low}$ macrophages engulfed significantly more PMN on average than CD11b$^{high}$ macrophages and the two populations were distinguished by an engulfment threshold of seven PMN. Example 4 shows that CD11b$^{low}$ macrophages may be considered "satiated", meaning that they lost their phagocytic potential upon meeting the apoptotic PMN engulfment threshold and reducing their CD11b expression.

To avoid potential residual effect of the apoptotic cells (AC) in the conditioned media, it is important that most AC is engulfed by the macrophages. Example 9 shows the effect of different ratios of CD11b$^{high}$ macrophages to AC, on the fraction of AC that remains after engulfment. A ratio of 1:1 left only 8% AC not engulfed, while higher macrophage/AC ratios of 1:1.5, 1:2 or 1:5 left more AC not engulfed.

Accordingly, in some embodiments the incubation of mononuclear cells in the presence of apoptotic cells is performed at a ratio of mononuclear cells to apoptotic cells of between 1:1 and 1:5. In some embodiments, the ratio between mononuclear cells and apoptotic cells is between 1:1 and 1:1.5. In some embodiments, the ratio between mononuclear cells and apoptotic cells is 1:1. In some embodiments incubation of mononuclear cells in the presence of apoptotic cells is performed for 16-24 hours. For example, the incubation with the apoptotic cells may take from 5 to 10, preferably 8, hours, followed by washing of the cells (e.g., with PBS), addition of fresh medium and further incubation for 10-15, preferably, 12, hours. In some embodiments the incubation of mononuclear cells in the presence of apoptotic cells is performed such that the average number of engulfed apoptotic cell per mononuclear cell is 7. In some embodiments incubation of mononuclear cells in the presence of apoptotic cells is performed in the presence of one or more anti-inflammatory agents such as, but not limited to, IL-10, TGFP, PPARX, ligand, vitamin D and its derivatives, glucocorticoid, or other pro-resolving lipid mediators.

In certain embodiments the apoptotic cells are polymorphonuclear cells. In some embodiment the apoptotic cells are neutrophils. In some embodiment the apoptotic cells are lymphocytes, e.g. T cells. Such cell populations may be produced by standard procedures known in the art. Apoptosis may be induced by a variety of well-known methods including but not limited to, incubation with staurosporine (e.g. 1 μM for 4 hr) or etoposide (0.5 ρM), or exposure to UV irradiation (e.g. 5 minutes). Apoptosis may also be induced in neutrophils by prolonged incubation (e.g. for 12-24 hours) in culture media in the absence of cytokines. Any type of apoptotic cells may be used such as apoptotic Jurkat T cells after treatment with staurosporine.

In some other embodiments, the agent used for reduction of the CD11b expression of macrophages is a pro-resolving lipid mediator. The pro-resolving lipid mediator may be selected from, without being limited to, a lipoxin (LX), a resolvin (Rv), a protectin (PD), a maresin (MaR), or a glucorticoid. Examples of such agents, without being limited to, are lipoxin LXB$_4$ and 15-epi-LXA$_4$, resolvins RvD1 and RvD2, protectin PD1, and dexamethasone.

Example 7 shows that resolvins (RvD1, RvE1) and glucocorticoids (Dex) enhanced the appearance of CD11b$^{low}$ macrophages and RvD1 and RvE 1, but not Dex, also reduced CD11b expression on CD11b$^{high}$ macrophages. The secretion of IL-10, a pro-resolving cytokine generated following the ingestion of apoptotic cells, was up-regulated by each of the pro-resolving mediators, in unstimulated and LPS-stimulated macrophages.

Thus, treatment with RvD1, RvE1, and Dex, promoted macrophage immune-silencing, as well as the secretion of pro-resolving cytokines from these cells. Example 8 shows that ex vivo treatment with the pro-resolving lipid mediators RvD1 or RvD2, the protectin PD1, the lipoxins LXB$_4$ or 15-epi-LXA$_4$, or dexamethasone (Dex), promotes macrophage switch to the CD11b$^{low}$ phenotype similarly to the effect of incubation with apoptotic cells. Therefore, such treatment can possibly either enhance the effect of incubating with apoptotic cells in order to enrich for CD11b$^{low}$ macrophages, or such treatment with pro-resolving lipid mediators may replace incubation with apoptotic cells.

In the last step of the method, the conditioned medium is collected from the culture of the CD11b$^{low}$ macrophages and further purified by standard procedures.

In a further aspect, the present invention relates to a pharmaceutical composition comprising the conditioned cell culture medium of CD11b$^{low}$ macrophages of the invention, or a biologically active fraction thereof, and a pharmaceutically acceptable carrier, excipient or diluent.

The conditioned medium of the present invention or prepared according to the methods of the present invention or fractions thereof can be administered to individuals in need per se or in a pharmaceutical composition with suitable carriers, excipients or diluents.

As used herein, the term "a biologically active fraction thereof" refers to a fraction of the conditioned cell culture medium of CD11b$^{low}$ macrophages obtained by fractionation of the conditioned medium and shown to retain the same biological activities as shown herein for the whole conditioned medium such as cytotoxic, anti-metastatic or anti-fibrotic activity. Conveniently, the biological activity may be determined using the three dimensional culture system that models tumor dormancy and breakout, e.g. as exemplified in the Examples section below. The fractionation of the conditioned medium may be carried out by standard procedures, e.g. organic extractions, size exclusion fractions and/or HPLC fractionation, as known in the art.

The term "pharmaceutically acceptable carrier" refers to a carrier or diluent that does not cause irritation or other adverse effect to an organism and does not have an adverse effect on the biological activity and properties of the administered compound. The "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active agents into preparations that can be used pharmaceutically. Proper formulation is dependent upon the route of administration chosen.

Suitable routes of administration may, for example, include oral, rectal, transmucosal, especially transnasal, intestinal, or parentersl delivery, including intramuscular, subcutaneous and intramedullary injections as well as intrathecal, direct intraventricular, intravenous, intraperitoneal, intranasal or intraocular injections.

Alternatively, the pharmaceutical composition may be administered in a local rather than systemic manner, for example, via injection directly into a tissue region of a patient.

For injection, the active ingredients of the compositions of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Pharmaceutical compositions suitable for use in context of the present invention include compositions wherein the active ingredients are contained in an amount effective to achieve the intended purpose. More specifically, a "therapeutically effective amount" means an amount of an active ingredient effective to prevent, alleviate or ameliorate symptoms of a disease or disorder or prolong the survival of the subject being treated.

Determination of a therapeutically effective amount is well within the capability of those skilled in the art, especially in light of the detailed disclosure provided herein.

Depending on the severity and responsiveness of the condition to be treated, dosing can be of a single or a plurality of administrations or a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The $CD11b^{low}$ macrophages or the conditioned media thereof may be re-infused (in the case of autologous treatment, or infused, in the case of an allogeneic treatment) into the patient (e.g. in a physiologic PBS solution) systemically, e.g. intravenously, by conventional clinical procedures. Patients may generally receive from about $10^6$ to about $10^{12}$ macrophages, depending on the condition of the patient. The macrophages administered are typically viable and may optionally be activated prior to administering to the subject (e.g. by treatment with corticosteroids, PPARγ agonists, TGFβ or vitamin D).

The conditioned cell culture medium of $CD11b^{low}$ macrophages, a biologically active fraction thereof or a pharmaceutical composition comprising them can be used for treatment of cancer or fibrosis.

The term "treating" or "treatment" as used herein includes abrogating, substantially inhibiting, slowing or reversing the progression of a condition, substantially ameliorating clinical symptoms of a condition or substantially preventing the appearance of clinical symptoms of a condition, With regard to cancer, the term refers to preventing or delaying cancer recurrence or occurrence of metastasis, inhibiting tumor growth or causing death of cancer cells, especially of metastatic cancer cells. Such treatment can also lead to regression of tumor growth, i.e., to decrease in size or complete regression of the tumor, and to elimination of metastases. The terms "tumor" and "cancer" are used interchangeably herein.

According to some embodiments, the treatment according to the present invention prevents the proliferation or outbreak of dormant tumor cells.

The terms "dormant cells" or "dormant tumor cells" as used herein relate to either of the two states that have been described regarding tumor dormancy. Dormant tumor cells may exist in a quiescent state for many years as solitary quiescent tumor cells as demonstrated by their negative staining for the proliferation marker Ki67 and their negative staining for apoptosis. Alternatively, tumor dormancy may exist as micrometastases where cellular proliferation is balanced by apoptosis. These micrometastases remain dormant because of lack of recruitment of the vasculature needed to nourish the tumor, known as the angiogenic switch and/or involvement of the adaptive immune system such as cytotoxic $CD8^+$ T cells.

In some embodiments of the invention, the treatment of cancer comprises inhibiting cancer metastasis.

The term "treating" or "treatment" as used herein with regard to fibrosis, refers to preventing the occurrence of fibrosis or inhibiting fibrosis by inhibiting the progress and/or the extent of the fibrotic process.

The term "fibrosis" as used herein, relates to a process in which excess fibrous connective tissue is formed in an organ or tissue in a reparative or reactive process. In the process of fibrosis, the connective tissue deposited can obliterate the architecture and function of the underlying organ or tissue. Fibrosis can happen in response to injury (scarring) or as part of a pathological process such as, for example, in liver disease, kidney disease, pulmonary fibrosis or heart failure.

In a further aspect, the present invention is directed to a culture of isolated $CD11b^{low}$ human macrophages or a cellular therapy preparation comprising said culture and a pharmaceutically active carrier, excipient or diluent, for use in the treatment of cancer or fibrosis.

In yet a further aspect, the present invention provides a method for treating cancer comprising administering to a subject in need an effective amount of an active agent selected from : (i) a conditioned cell culture medium of $CD11b^{low}$ macrophages; (ii) a biologically active fraction thereof; (iii) a pharmaceutical composition comprising (i) or (ii) and a pharmaceutically active carrier, excipient or diluent; (iv) a culture of human $CD11b^{low}$ macrophages; or (v) a pharmaceutical composition comprising (iv) and a pharmaceutically active carrier, excipient or diluent, wherein said treatment comprises preventing or delaying cancer recurrence or occurrence of metastasis or inhibiting cancer metastasis.

The types of cancer that can be treated by the method of the invention are typically cancers that relapse, meaning that the patient can be in remission, that is, free of active disease, but the cancer may become active again. As explained above, recurrence of the disease is generally due to the presence of dormant cells which may become activated. Additionally, treatment-eligible tumors are also those which metastasize.

Accordingly, in some embodiments, the active agents of the invention may be used to prevent and treat recurring metastatic cancers. It is also appreciated that they can be used also for treatment of patients with an active cancer, for example, to prevent further metastases or inhibit the level of tumor spreading.

In some embodiments, the cancer is selected from breast, prostate, esophageal, skin, lung, head and neck, colon or liver cancer. In some embodiments, the cancer is breast cancer.

In some embodiments, the cancer is resistant to chemotherapy, immunotherapy, anti-angiogenic therapy and/or radiotherapy. In some embodiments, the cancer is resistant to chemotherapy and/or radiotherapy. In some embodiment the cancer is resistant to hormone responsive therapy. For example, the compositions and methods of the invention may be suitable for the treatment of heterogeneous hormone responsive tumors (e.g. breast or prostate tumors), which are not amenable for treatment with conventional hormone responsive therapies since the respective receptors are not expressed on substantially all the tumor cells. Advantageously, the treatments of the invention may be used for treatment of triple-negative breast cancer, i.e. breast tumors not expressing the genes for estrogen receptor (ER), progesterone receptor (PR) and Her2/neu, which are thus not amenable for treatment with hormone-responsive therapies. Often, such triple negative breast tumors are also resistant to immuno-therapies (e.g. Herceptin) or treatment with small molecules (e.g. Lapatinib.

Optionally, the active agents or compositions of the invention may be administered to the subject in combination (concurrently or sequentially) with other anti-cancer agents or treatments. For example, they may be administered in combination with one or more chemotherapeutic agents such as, but not limited to, alkylating agents, e.g. Cyclophosphamide, Ifosfamide, Melphalan, Chlorambucil, BCNU, CCNU, Decarbazine, Procarbazine, Busulfan, and Thiotepa; antimetabolites, e.g. Methotraxate, 5-Fluorouracil, Cytarabine, Gemcitabine, 6-mercaptopurine, 6-thioguanine, Fludarabine, and Cladribine; anthracyclins, e.g. daunorubicin. Doxorubicin, Idarubicin, Epirubicin and Mitoxantrone; camptothecins, e.g. irinotecan and topotecan; taxanes, e.g. paclitaxel and docetaxel; and platinums, e.g. Cisplatin, carboplatin, and Oxaliplatin, as well as to immunotherapies, e.g. Herceptin and Cetuximab, hormone responsive therapies, e.g. Tamoxifen, Raloxifene, Fulvestrant, Anastrozole, Letrozole or Exemestane for breast cancer, or anti-androgens e.g. flutamide for prostate cancer, small molecules inhibiting epidermal growth factor receptor (EGFR, e.g. Lapatinib or gefitinib), anti-angiogenic therapy, e.g. Bevacizumab, sunitinib, sorafenib and pazopanib, antibodies and small molecules targeted against beta 1 integrins (e.g. ATN-161, Voloximab and JSM6427), or inhibitors, antagonists and small molecules against urokinase receptor (UPAR).

Advantageously, the compositions of the invention may be used in conjunction (concurrently or sequentially) with surgery or radiotherapy. For example, the cells or cell-free preparations of the invention may be used concomitantly with, or within 1-4 days of, a surgical treatment for cancer. Dissemination of tumor cells, which are the source for the recurrence and progression to metastatic disease, may occur as a result of the surgical operation. By performing such procedures in conjunction with the compositions of the invention, cancer recurrence or metastasis may be prevented or inhibited. Thus the compositions and methods of the invention may be used to inhibit post-surgery metastatic process.

Given that dissemination of tumor cells may have already occurred even at an early stage of tumor progression, the anti-cancer agents or treatments that may be administered in combination with the compositions of the invention, include, in some embodiments, neoadjuvant treatment, namely radiotherapy, chemotherapy, hormone therapy and/or immunotherapy used for shrinking the size of the tumor prior to surgical operation.

In yet a further aspect, the present invention provides a method for treating fibrosis comprising administering to a subject in need an effective amount of an active agent selected from : (i) a conditioned cell culture medium of $CD11b^{low}$ macrophages; (ii) a biologically active fraction thereof; (iii) a pharmaceutical composition comprising (i) or (ii) and a pharmaceutically active carrier, excipient or diluent; (iv) a culture of human $CD11b^{low}$ macrophages; or (v) a pharmaceutical composition comprising (iv) and a pharmaceutically active carrier, excipient or diluent, wherein said treatment of fibrosis comprises preventing or inhibiting fibrosis.

Examples 15 and 16 hereinafter show that development of fibrosis can be the cause of activation and proliferation of dormant tumor cells. Since the active agents of the invention can prevent the process of fibrosis, they also prevent proliferation of the dormant tumor cells. Thus, treatment of the fibrosis associated with cancer is encompassed by the present invention.

Examples 10-14 show that conditioned medium of $CD11b^{low}$ macrophages can inhibit proliferation of fibroblasts and their differentiation into myofibroblasts induced by TGFβ, including inhibiting expression of α-SMA and deposition of Col-I, which marks the process of fibrosis. These results demonstrate for the first time that conditioned medium of $CD11b^{low}$ macrophages can prevent fibroblasts from differentiation into myofibroblasts and secretion of Col-I. Without being bound to any theory, the inventors believe that these results indicate that these macrophages may secrete anti-fibrotic factors that can prevent the establishment of a fibrotic microenvironment.

Accordingly, in some embodiments, the fibrosis is associated with a disease or a condition selected from acute lung injury, Alzheimer's disease, chronic diabetic wounds, chronic granulomatous disease (CGD), chronic obstructive pulmonary disease (COPD), constrictive pericarditis, Dupuytren's disease, emphysema, hypertrophic burn scars, keloid, liver cirrhosis, plantar fibromatosis, retinal detachment inflammation, scleroderma, cystic fibrosis, endometrial fibrosis, idiopathic pulmonary fibrosis, myocardial fibrosis, nephrogenic fibrosis, pancreatic fibrosis, perineural fibrosis, renal interstitial fibrosis, secondary fibrosis in the gastrointestinal tract or fibrosis resulting after surgery.

The following examples are presented in order to more fully illustrate some embodiments of the invention. They should, in no way be construed, however, as limiting the scope of the invention.

EXAMPLES

Materials and Methods

Reagents

ELISA kits for mouse TNF-α, IL-1β, IL-10, TGFβ, CCL2, CCL3, and CCL5 ere obtained from R&D Systems. CFSE, staurosporine, LPS (from *Escherichia coli*, clone 055:B5), PKH2-PCL green fluorescence linker kit, and dexamethasone (Dex) from Sigma. Poly (I:C) and CpG-ODN from InvivoGen. RvE1 (5S,12R,18R-trihydroxy-4Z, 8E,10E,14Z,16E-eico sapentaenoic acid) and RvD1 (7S,8R, 17S-trihydroxy-4Z,9E,11E,13Z,15E,19Z-docosahexaenoic acid) were obtained from Cayman Chemicals and the synthetic Rv were matched according to the previously published biological and physical material, PD1, LXB$_4$, or 15-epi-LXA$_4$ were a gift from Prof. Serhan, Harvard.

Isolation and Culture of Human Monocytes

PBMC is obtained following informed consent from individual/patient by Ficoll density centrifugation (400 g, 30 min, without brake), and is washed three times with RPMI. Monocytes are further purified by adherence: cell pellet is resuspended in culture media (RPMI 1640, supplemented with 10% human serum, 2 mM L-glutamine, 100 µg/ml streptomycin, and 100 units/ml penicillin) and 10×10$^6$ cells per well are transferred to 6-well plates, and incubated horizontally for 1.5 hrs at 37° C. in 5% CO$_2$, humidified environment. Then, nonadherent lymphocytes are discarded and the plates are washed gently with fresh RPMI.

The isolated monocytes are then collected and differentiated to macrophages either with 10% autologous serum or with MCSF.

Murine Peritonitis

Male C57BL/6 mice (6-8 wk) were injected intraperitonealy (I.P) with zymosan A (1 mg). 66 hours post zymosan A injection, the mice were euthanized by CO$_2$, their peritoneal cavity was lavaged with 5 ml of phosphate buffered saline (PBS) and the peritoneal exudates were collected by centrifugation for further analysis and experimentation.

Peritoneal exudates were collected and exudate cells were stained with FITC-conjugated rat anti-mouse Ly-6G, PE-conjugated rat anti-mouse F4/80, and PerCP-conjugated rat anti-mouse CD11b (Biolegend) and analyzed by FACSCalibur (Beckton-Dickinson). Macrophages were isolated using EasySep PE selection magnetic beads following the manufacturer's instructions (StemCell Technologies).

In some experiments, the macrophages were sorted to CD11b$^{high}$ and CD11b$^{low}$ populations of >95% purity, using FACSaria (Beckton-Dickinson), and the separate populations were used for microscopic analysis and for ex vivo stimulation. In some experiments, PKH2-PCL green (0.25 mM, 0.5 mL) was injected I.P at 48 h and peritoneal cells were recovered 4 h later, immunostained for F4/80 and CD11b as above and analyzed for fluorescence intensity of different macrophage populations. In relevant experiments, vehicle, RvD1, RvE1 (100 ng/mouse each), or Dex (25 mg/mouse) were introduced to the peritoneum 48 h after peritonitis initiation, and the exudates were recovered after 66 h and analyzed as before.

Western Blot Analysis for CD11b$^{high}$ and CD11b$^{low}$ Macrophages

Protein extracts of sorted populations (>95% purity) of CD11b$^{high}$ and CD11b$^{low}$ macrophages were run using 10% SDS-PAGE (50 µg/lane), transferred to nitrocellulose membranes, and immunoblotted with either goat anti-mouse CD11b (Santa-Cruz Biotechnology), rabbit anti-mouse iNOS (Abcam), goat anti-mouse arginase-1 (Abcam), rabbit anti-mouse COX-2 (Cayman Chemicals), sheep anti-mouse 12/15-LO (Cayman Chemicals), goat anti-mouse MMP-9 (R&D Systems), goat anti-mouse β-actin (Santa Cruz Biotechnology) or goat anti-mouse tubulin (Santa Cruz Biotechnology). Then, the membranes were washed and incubated with the appropriate HRP-conjugated secondary antibody. The blots were washed and developed using EZ-ECL (Biological Industries).

Macrophage Transfer

Macrophages were isolated from peritoneal exudates 48 h post-peritonitis initiation, stained with CFSE (1 mM), and injected into the peritoneum of mice that underwent peritonitis for 4 h. After an additional 18 h, cells from peritoneal exudates, inguinal lymph nodes (LN), and spleen were recovered from the recipient mice, immunostained as above, and the percentage of CD11b$^{high}$ and CD11b$^{low}$ macrophages in each site was determined.

Confocal Microscopy

Sorted CD11b$^{high}$ and CD11b$^{low}$ macrophages were isolated and loaded with 50 nm LysoTracker Red DND 99 dye (Molecular Probes) for 2 h at 37° C. in RPMI. Cells were then fixed with 2% paraformaldehyde at room temperature and stained with Hoechst (Molecular Probes) and FITC-conjugated anti-mouse Ly-6G. Mounted slides were kept in the dark at 4° C. until analyzed by confocal microscopy. Confocal images were acquired using Z-sections of 1 µm thickness. The images were processed with Zeiss LSM Image Browser software.

Apoptotic PMN (Polymorphonuclear) Engulfment Enumeration

Exudate cells or sorted CD11b$^{high}$ and CD11b$^{low}$ macrophages were stained with Hoechst, and enumerated under a fluorescent microscope (Zeiss). Two areas of two cover slips, each containing at least 50 (overall 200) macrophages were analyzed, and the average number of PMN engulfed per macrophage as well as the number of macrophages with cutoff numbers of engulfed PMN, were calculated. In sorted cells, F4/80$^+$, Ly-6G$^+$ entities (identified as macrophages that are attached to but did not fully engulf a PMN by forward versus side scatter analysis) were excluded from the samples to avoid counting of attached PMN.

TLR-Mediated Responsiveness Ex Vivo

Exudate macrophages were sorted or separated using PE selection magnetic beads (StemCell Technologies) and incubated (1×10$^6$ cells in 0.5 mL of culture media) with LPS (0-1000 ng/mL), poly (I:C) (4 µg/mL), or CpG-ODN (1 µM). After 16 h, the supernatants were collected and their TNF-α, IL-β, IL-10, TGFβ, CCL2, CCL3, and CCL5 contents were determined by standard ELISA.

Regulation of Macrophage Phenotype by Apoptotic Cells Ex Vivo

Jurkat cells (T lymphocyte cell line) were treated with 1 mM staurosporine (4 h, Sigma) to induce apoptosis and washed. Then, peritoneal macrophages or sorted subpopulations thereof were incubated in the presence or absence of apoptotic Jurkat cells (1:5 macrophage to apoptotic cell ratio). At the beginning of the incubation and after 20 h, macrophages were immunostained for CD11b and analyzed by FACS analysis. Alternatively, protein extracts were prepared from the macrophages after the incubation period and run by SDS-PAGE followed by western blot analysis for CD11b, arginase-1, 12/15-LO, actin, and tubulin, as above.

Cell Line Cultures

Mouse mammary cancer cells D2.0R (obtained from Prof. Ann F. Chambers, described in Morris et al., *Clinical & Experimental Metastasis* 1993, 11(1):103-112), Mouse Embryonic Fibroblast (MEF) cell line (obtained from Dr. Sarit Larisch, Haifa University, Haifa, Israel) were maintained in DMEM high glucose (GIBCO), 10% fetal bovine serum (FBS), and 1% penicillin-streptomycin at 37° C., 5% $CO_2$ incubator. Jurkat T cells (obtained from Prof. Debbie Yablonski, Technion, Israel) were maintained in RPMI-1640 (GIBCO) high glucose, 10% fetal bovine serum (FBS), and 1% penicillin-streptomycin at 37° C., 5% CO2 incubator.

Fibroblasts differentiation to myofibroblasts was promoted as follows: Mouse embryonic fibroblasts (MEFs) were culture in DMEM 10% FBS medium in 6 well plates. The next day the cells were overlaid with RPMI containing 1% penicillin-streptomycin media for overnight incubation. Thereafter the cells were treated with RPMI 10% FBS medium containing 1 ng/ml TGFβ1 for 48-72 hours (PeproTech, Israel).

Animals 7-8 weeks old male C57BL mice were purchased from Harlan Biotech Israel and maintained under special pathogen-free conditions in the animal facility at the Gutwirth Science Park in the Technion (Israel Institute of Technology, Haifa).

Apoptotic Cells Preparation

Apoptosis was initiated in Jurkat T cells by treating the cells with staurosporine (1 µg/ml; Sigma-Aldrich) for 4 hours. Then the cells were washed twice with PBS, re-suspended in RPMI 10% FBS medium and added to the plated macrophages.

Ex-Vivo Generation of Pro-Resolving $CD11b^{low}$ Macrophages

The isolated macrophages (Mφ) were incubated with apoptotic Jurkat T cells (AC). $5 \cdot 10^6$ cells were used at the following Mφ to AC ratios of: 1:1, 1:2 and 1:5, respectively. After 8 hours of incubation the cells were washed with PBS and overlaid with fresh RPMI 10% FBS medium for additional 12 hours of incubation. Next, conditioned medium was collected and the macrophages were further characterized for their conversion to $CD11b^{low}$ phenotype by determining their surface expression of CD11b by FACS analysis.

FACS Analysis

Determining surface expression of CD11b was carried out as follows: Exudates were blocked with FcR blocker (anti-CD16/CD32; Biolegend) mAb (0.5 µg/$0.5 \times 10^6$ cells), and co-stained with PE-conjugated anti mouse F4/80 (Cat #12216) (0.5 µg/$0.5 \times 10^6$ cells) and PerCP-conjugated anti-mouse CD11b (Cat #101230) (0.5 µg/$0.5 \times 10^6$ cells) for 20 min at 4° C. Then, cells were washed with FACS Buffer (1% BSA in PBS) and analyzed by FACSCanto ii (BD Biosciences) and FACSDiva software.

Western Blot Analysis for MEFs

MEFs were lysed in WCE (whole-cell extract) buffer [25 mM Hepes, pH 7.7, 0.3M NaCl, 1.5 mM MgCl2, 0.2 mM EDTA, 0.1% Triton X-100, 100 µg/ml PMSF and protease inhibitor cocktail (Rosche, 1:100 dilution)]. The proteins were separated by SDS-PAGE (8-10%) followed by transfer on to a nitrocellulose membrane. The membrane was blocked with 5% (w/v) non-fat dried skimmed milk powder in PBS supplemented with 0.05% Tween20 (PBS-T) for 1 hour at room temperature (R.T). Membrane was then probed either with mouse anti α-SMA (Cat #ab7817; Abcam), or with rabbit anti-mouse GAPDH (Cat #sc25778; Santa Cruz Biotechnology) at 4° C. overnight.

Next, the membrane was incubated with the appropriate HRP-conjugated secondary antibody, for 1 hour at R.T. and washed 15 min×3 with PBS-T, WesternBright ECL (Advansta) was added to the membrane for 30 seconds and analyzed using ImageQuant LAS-4000 analyzer (GE Healthcare Life Sciences) & "ImageQuant LAS-4000" software (GE Healthcare Life Sciences). Densitometry analysis was performed using ImageQuant total lab 7 (GE Healthcare Life Sciences), an image analysis software.

Three-Dimensional Cell Cultures

D2.0R stably expressing Green Fluorescence protein (D2.0R-GFP cells) and MEF cells were harvested from their growth plates using 0.25% trypsin EDTA. Collected cells were cultured in Cultrex® growth factor reduced Basement Membrane Extract (BME: Trevigen, Inc) as follows: An 8-well chamber glass slide system (Lab-TEK® II, Naperville, Ill.) was coated with 50 µl Cultrex® (Basement membrane Extract; BME) (Barkan et al., 2010a) (protein concentration between 15 mg/ml; thickness 1-2 mm). $5 \times 10^3$ cells/well of D2.0R-GFP cells, and $6 \times 10^4$ MEF cells were re-suspended in DMEM low glucose supplemented with 2% FBS and 2% Cultrex® and either cultured separately or co-cultured on the coated slides. Slides were incubated at 37° C., 5% $CO_2$ incubator. Cell morphology was monitored by light microscopy.

Immunofluorescence Staining in Cell Culture

Cells cultured in 8-well chamber glass slides in 2 dimensional culture or in 3 dimensional culture, were fixed and treated for 5 minutes with 4% Paraformaldehyde (PFA) containing 5% sucrose and 0.1% Triton X-100, and re-fixed for an additional 25 minutes with cold acetone for 10 minutes. The cells were washed for 10 minutes with PBS and an additional 15 minutes with PBS containing 0.05% Tween 20 (Sigma). Next, fixed cells were blocked with IF buffer (130 mM NaCl, 7 mM Na2HPO4, 3.5 mM NaH2PO4, 7.7 mM NaN3, 0.1% BSA, 0.2% Triton X-100, 0.05% Tween 20) contain 10% donkey serum for 1 hour and incubated overnight at 4° C. with goat anti type I collagen (1:100) (Cat #1310-01; SouthernBiotech) together with Alexa Fluor® 488 phalloidin (1:40; Molecular Probes). The cells were washed three times with PBS for 15 minutes each, and incubated for 1 hour with donkey anti goat conjugated to Alexa Fluor® 649, (Invitrogen) at R.T. Next, the cells were washed as mentioned above and mounted with VECTASHIELD mounting medium with 4',6-diamidino-2-phenylindole (DAPI). The slides were imaged using a Nikon A1-R confocal laser scanning microscope (Haifa University, Haifa, Israel).

Apoptosis Detection

MEF cell line were cultured as described above in 8 well chamber glass slides, fixed with 4% PFA containing 5% sucrose and incubated for 1 hour with a mixture of TUNEL reaction mix according to the manufacturer's protocol (In Situ Cell death Detection Kit; TMR Red) covered with aluminum foil and placed in the 37° C., 5% $CO_2$ incubator for 1 hour. Next, the slides were washed three times with PBS for 15 minutes each, and mounted with VECTASHIELD mounting medium with DAPI. The slides were imaged using a Nikon A1-R confocal laser scanning microscope (University of Haifa, Haifa, Israel).

Proliferation Assay

MEF cells were cultured in 96 wells plate ($1.5 \times 10^3$ Cells/well). At indicated time points the CellTiter 96 AqueousOne Solution cell proliferation assay kit (Promega) was added to the wells for 2 hours to measure cell proliferation according the manufacturer's instructions. The absorbance was recorded at 490 nm.

2Images Analysis 3 images were captured from each well. Each captured frame was analyzed using NIS-Elements AR software to measure in the defined area the number of cells with positive DAPI staining, co-staining for DAPI and TUNEL (selected cells were larger than 8 μm), or Col-I expression by measuring sum intensity of area stained for Col-I per captured field.

3D Images Analysis

Confocal images were acquired using Z-sections of 1 □m thickness. Three images comprised of 15 Z-stacks images were captured from each well. Each Z-stack was analyzed using NIS-Elements AR software to measure sum intensity of area stained for Col-I.

Statistical Analyses

Ex vivo and in vivo experiments were performed at least three times with at least four replicates. Results were analyzed by one-way analysis of variance (for multiple groups) or Student's t-test (for comparison between two groups, used for proliferation assays, TUNEL assay, densitometry for W.B membranes and quantification of Col-I) with statistical significance defined as $P\leq0.05$ (*), $P\leq0.001$ (), or $P\leq0.0001$ (*).

Example 1

Figure 1A:
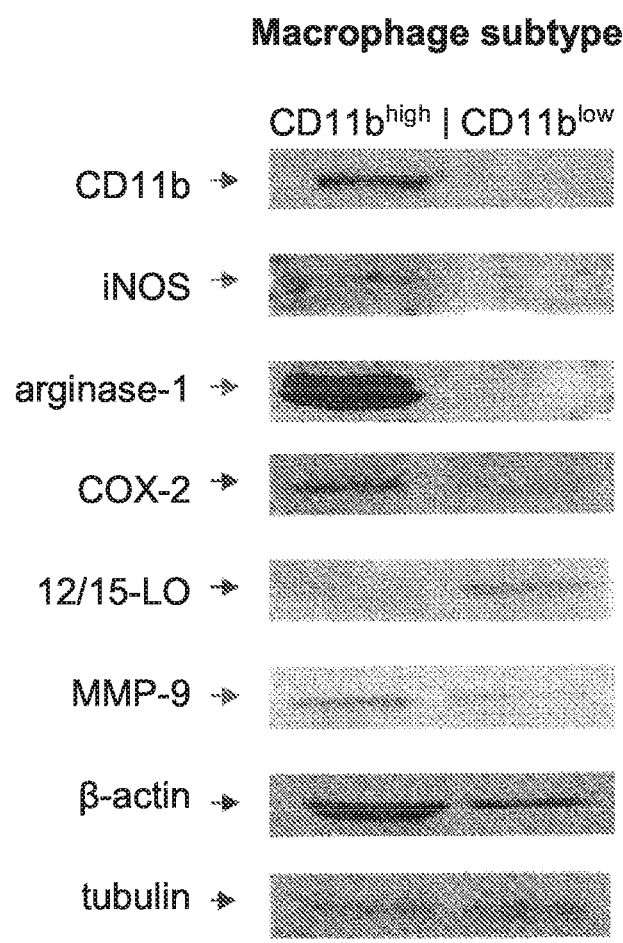
FIGS. 1A-1B show that $CD11b^{low}$ macrophages differ in their protein expression signature from $CD11b^{high}$ macrophages. Resolving peritoneal exudates were recovered 66 hours after zymosan A (1 mg) injection into mice, the cells were immunostained for Ly-6G, F4/80, and CD11b, and the Ly-6G$^-$/F4/80$^+$ macrophages were sorted to $CD11b^{high}$ and $CD11b^{low}$ populations. The recovered macrophages were lysed and their protein content was analyzed by SDS-PAGE and Western blotting for CD11b, iNOS, arginase-1, COX-2, 12/15-LO, MMP-9, and β-actin. Tubulin was used a loading control. Results are shown as representative blots (A) and mean±SE of three independent experiments (B). Fold difference in expression was calculated according to the following formula: Densitometric units (DU) of $CD11b^{high}$ extract/DU of $CD11b^{low}$ extracts from three experiments. Significant differences by Student's t test between $CD11b^{high}$ and $CD11b^{low}$ extracts (* P value<0.05,  P value<0.005, * P value<0.001) are indicated.
Figure 1B:
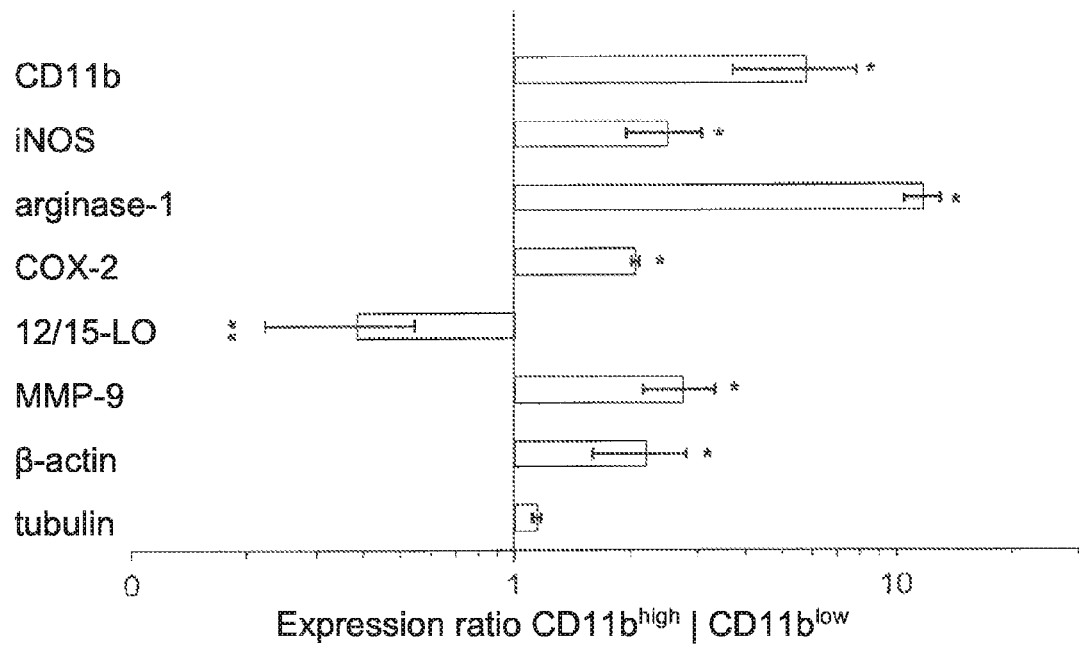

Characterization of Protein Expression Profile and Differentiation Markers of $CD11b^{low}$ and $CD11b^{high}$ Macrophages Macrophages positive for the macrophage differentiation marker F4/80 obtained from mouse peritoneal exudates following induction of peritonitis were characterized and sorted according to their CD11b expression as detailed above. It was found that at 66 h after peritonitis initiation, 70% of the exudate cells were macrophages, of which 17% expressed low levels of CD11b ("$CD11b^{low}$"). As can be seen in FIG. 1A, top panel and FIG. 1B, the expression of CD11b on $CD11b^{high}$ macrophages was tenfold higher than its expression on $CD11b^{low}$ macrophages, and the amount of CD11b in protein extracts of $CD11b^{low}$ macrophages was significantly lower than its amount in the extracts from $CD11b^{high}$ macrophages. The calculation of the fold difference in expression was calculated according to the following formula: densitometric units (DU) of $CD11b^{high}$ extract/DU of $CD11b^{low}$ extracts from three experiments.

Analysis of some proteins that are functionally relevant to inflammation and well-characterized by their expression in classically (M1)- and alternatively (M2)-activated macrophages was performed in $CD11b^{high}$ and $CD11b^{low}$ macrophages. The analysis has shown (FIGS. 1A, 1B) that $CD11b^{high}$ macrophages express low levels of iNOS, moderate levels of COX-2 and MMP-9 and high levels of arginase-1, but no 12/15-LO, whereas $CD11b^{low}$ macrophages express low levels of COX-2 and MMP-9, moderate levels of 12/15-LO and no iNOS or arginase-1. $CD11b^{low}$ macrophages lysates contained lower levels of actin than $CD11b^{high}$ cells, suggesting a modulation of cytoskeletal dynamics in these cells. Another housekeeping gene—tubulin—was equally expressed in both protein extracts indicating equal protein loading.

Further analysis have shown that the macrophage differentiation marker F4/80was expressed to a higher extent on $CD11b^{high}$ macrophages, further indicating that these cells possess different properties in comparison to $CD11b^{low}$ macrophages (data not shown).

Further analysis of surface receptor expression revealed reduced expression of CD206 and CD163 (both M2 markers) on $CD11b^{low}$ macrophages, in comparison to their $CD11b^{high}$ counterparts (19- and 17-fold difference, respectively; N=3, data not shown).

Thus, $CD11b^{high}$ and $CD11b^{low}$ macrophages display different expression profiles of functional proteins and differentiation markers.

Example 2

Engulfment of Apoptotic Polymorphonuclear Cells (PMN) by $CD11b^{low}$ Macrophages To examine whether $CD11b^{low}$ macrophages differ in their efferocytosis capacity from $CD11b^{high}$, sorted $CD11b^{high}$ and $CD11b^{low}$ macrophages were stained with Hoechst and LysoTracker, analyzed by confocal microscopy, and photographed (not shown). Similar preparations were enumerated for apoptotic PMN uptake, and analyzed according to average neutrophils engulfed per macrophage (N/M), and percentage of cells reaching engulfment threshold or engulfing an indicated number of apoptotic PMN. The results are shown in FIGS. 2A-C.

Figure 2A:
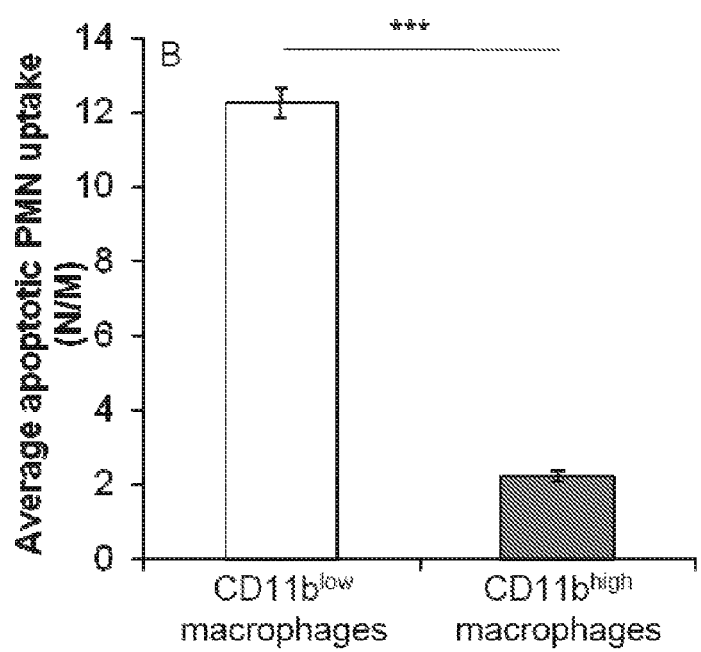
FIGS. 2A-2C show that $CD11b^{low}$ macrophages engulf higher numbers of apoptotic neutrophils than $CD11b^{high}$ macrophages. Sorted $CD11b^{high}$ (black bars and black boxes) and $CD11b^{low}$ (white bars and white diamonds) macrophages were stained with Hoechst and LysoTracker, analyzed by confocal microscopy, enumerated for apoptotic PMN uptake and analyzed according to average (A) neutrophils engulfed per macrophage (N/M), and percentage of cells reaching engulfment threshold of N/M=7 (B) or engulfing the indicated number of apoptotic PMN (C). Results are mean±SE (A, B) or representative (C) from three experiments. Significant differences by Student's t test between $CD11b^{high}$ and $CD11b^{low}$ macrophages (* P value<0.05,  P value<0.005, * P value<0.001) are indicated.
Figure 2B:
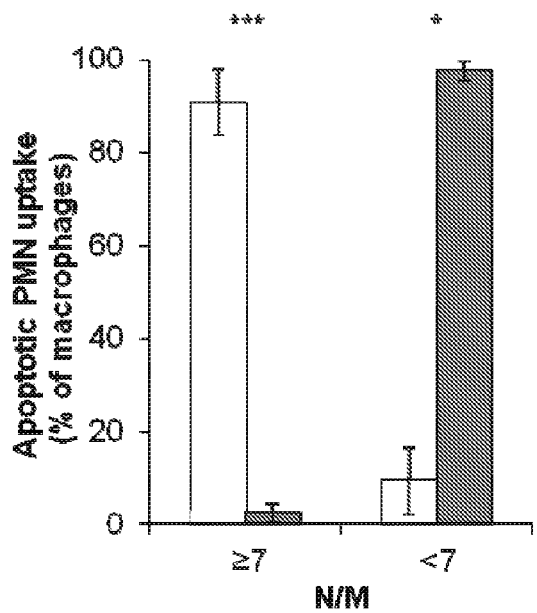
Figure 2C:
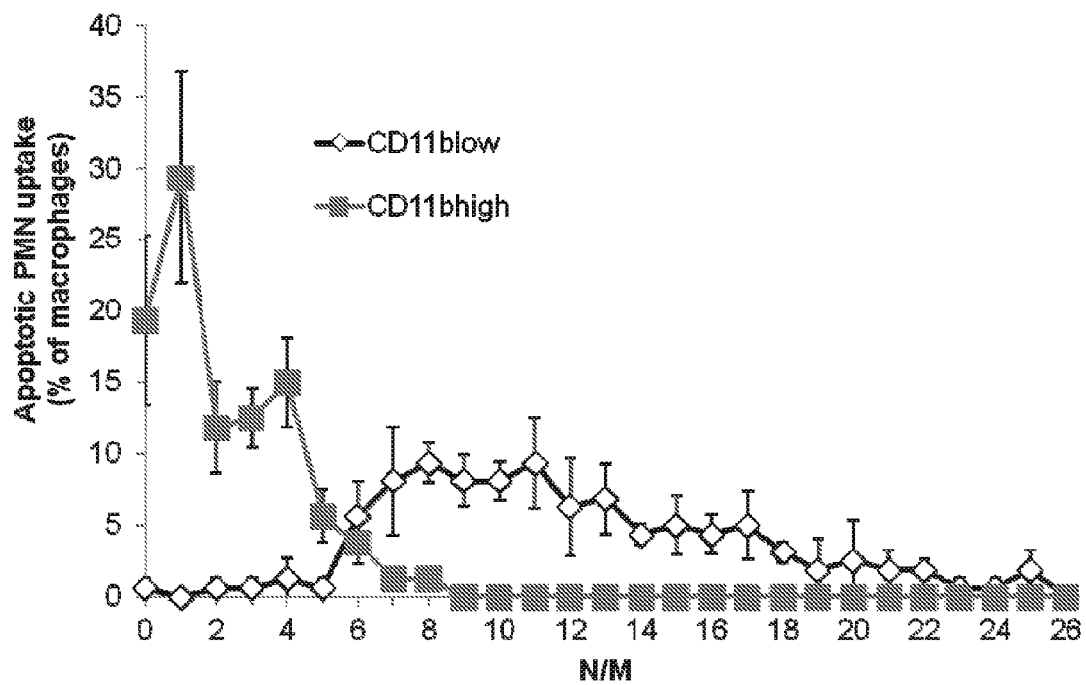

The analysis has shown that $CD11b^{low}$ macrophages engulfed significantly more PMN on average than $CD11b^{high}$ macrophages (12.2±0.2 N/M and 2.2±0.2 N/M, respectively, see FIG. 2A). LysoTracker staining indicated that the apoptotic PMN visualized in macrophages were indeed phagocytosed and not merely attached to the macrophage surface. In fact, in this experimental setting, $CD11b^{high}$ and $CD11b^{low}$ macrophages were distinguished by an engulfment threshold of seven PMN (FIG. 2B): 90.6±4.2% of the $CD11b^{low}$ macrophages engulfed seven or more PMN, whereas 97.5±1.2% of the $CD11b^{high}$ macrophages engulfed less than seven PMN. The results shown in FIG. 2C indicate that the differences between $CD11b^{high}$ and $CD11b^{low}$ macrophages in terms of engulfment of apoptotic PMN are distinct not only when engulfment thresholds are depicted but rather that there is very little overlap between the populations. Consequently, the threshold of engulfment is enforced in a very narrow range and hence, in this experimental setting only macrophages that engulfed six PMN have the same tendency to be either $CD11b^{high}$ or $CD11b^{low}$ macrophages.

Example 3

Figure 3A:
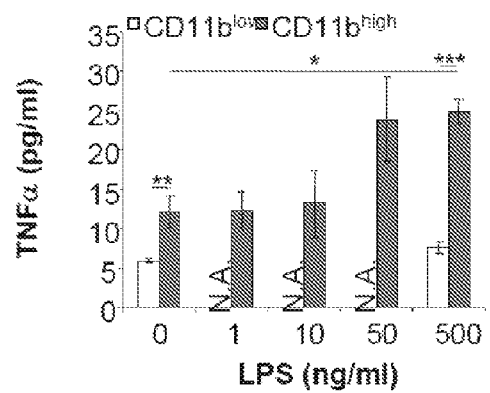
FIGS. 3A-3G show that $CD11b^{low}$ macrophages secrete lower levels of pro-inflammatory cytokines and chemokines, but higher levels of TGFβ in comparison to $CD11b^{high}$ macrophages. Sorted $CD11b^{high}$ (black bars in A, B) and $CD11b^{low}$ (white bars in A, B) macrophages were activated with lipopolysaccharide (LPS) at the indicated concentrations (A-B) or at 1 µg/ml (C-G), and evaluated for secreted TNFα (A), IL-1β (B) IL-10 (C), TGFβ (D), CCL2 (E), CCL3 (F), and CCL5 (G) using standard ELISA. Results are mean±SE of four replicates from a representative of three experiments. N.A.: not available.
Figure 3B:
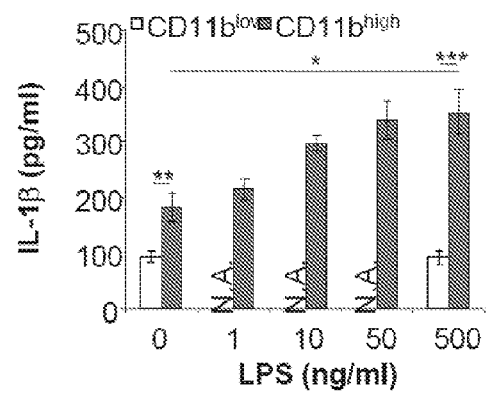
Figure 3C:
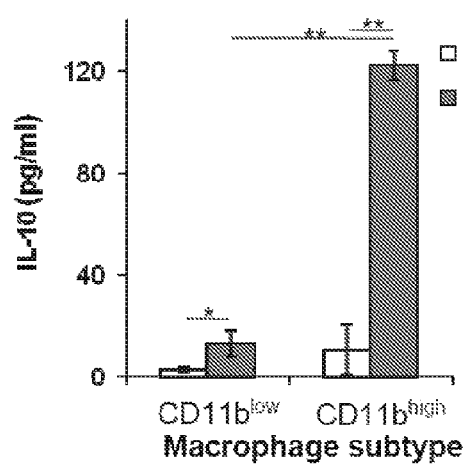
Figure 3D:
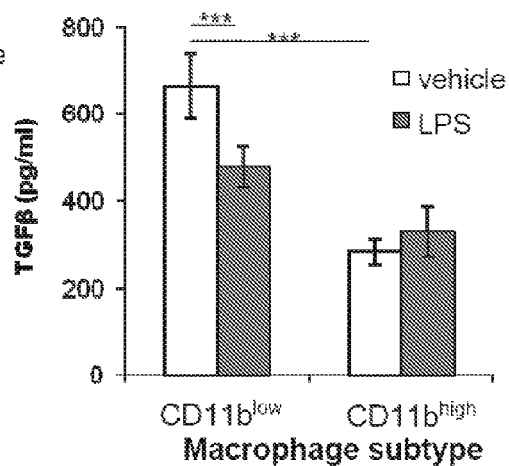
Figure 3E:
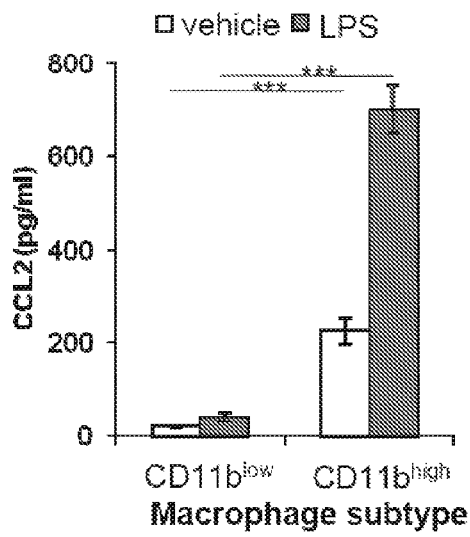
Figure 3F:
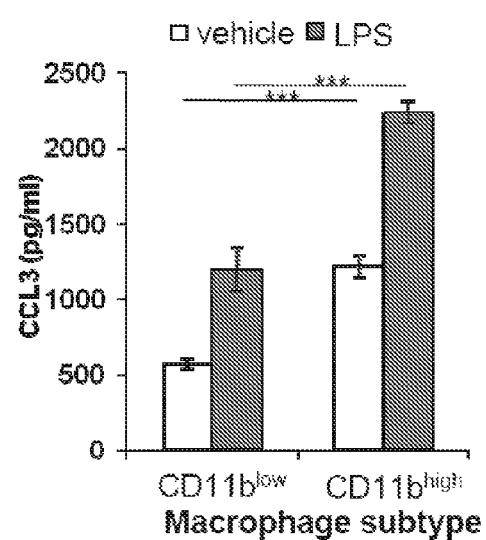
Figure 3G:
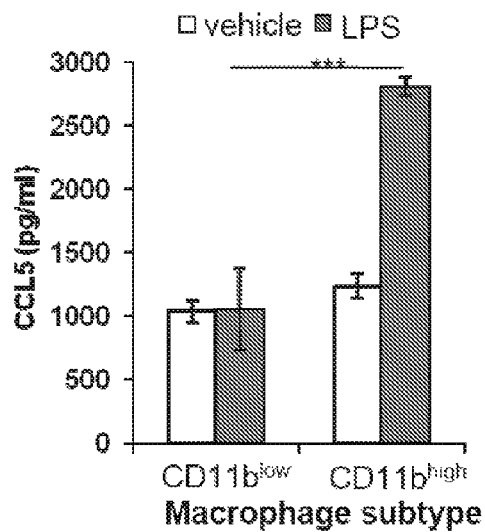
Figure 4A:
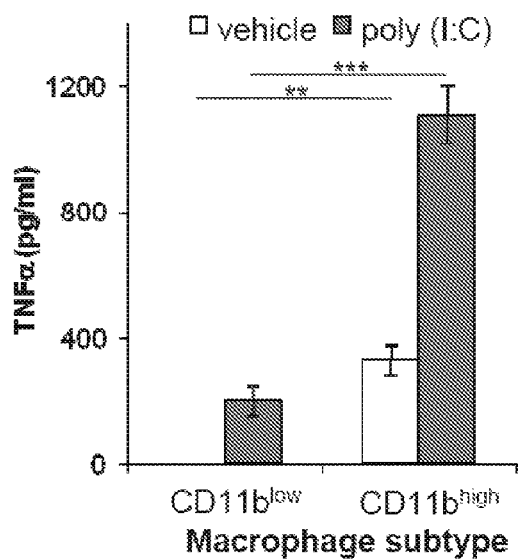
FIGS. 4A-4D shows that CD11b$^{low}$ macrophages secret lower levels of pro-inflammatory cytokines in response to various Toll-like receptor (TLR) ligands. Sorted CD11b$^{high}$ and CD11b$^{low}$ macrophages were not activated (added vehicle, white bars), activated with poly (I:C) (4 mg/ml; A-B), or with CpG-ODN (1 mM; C-D) (black bars) and evaluated for secreted TNFα (A,C) or IL-1β (B,D) using standard ELISA. Results are mean±SE of four replicates from a representative of three experiments. Significant differences by Student's t test between CD11b$^{high}$ and CD11b$^{low}$ macrophages or between macrophages stimulated with vehicle, poly (I:C), or CpG-ODN (* P value<0.05,  P value<0.005, * P value<0.001) are indicated.
Figure 4B:
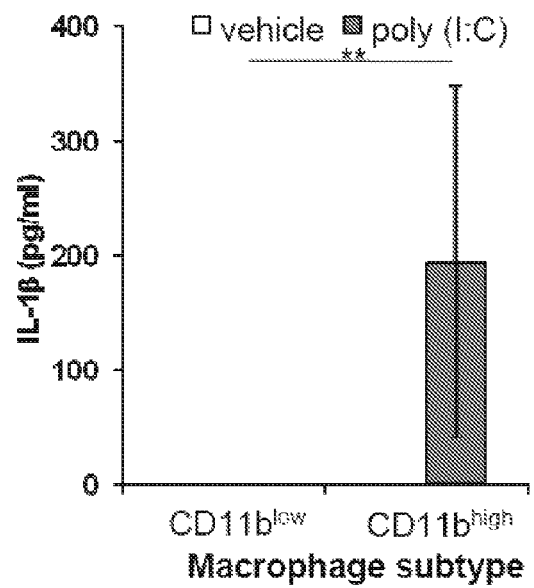
Figure 4C:
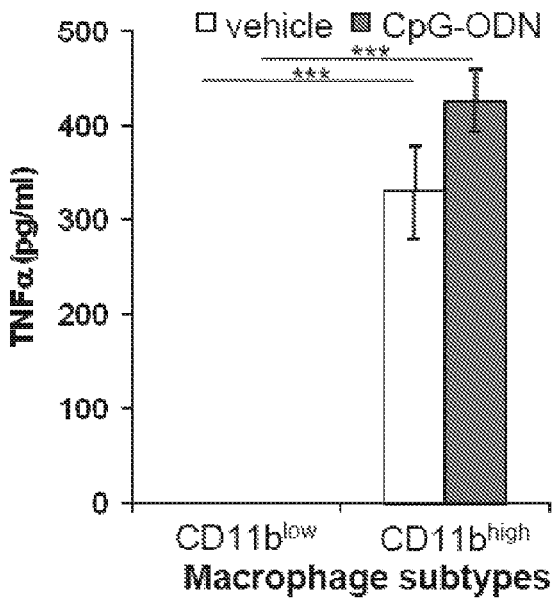
Figure 4D:
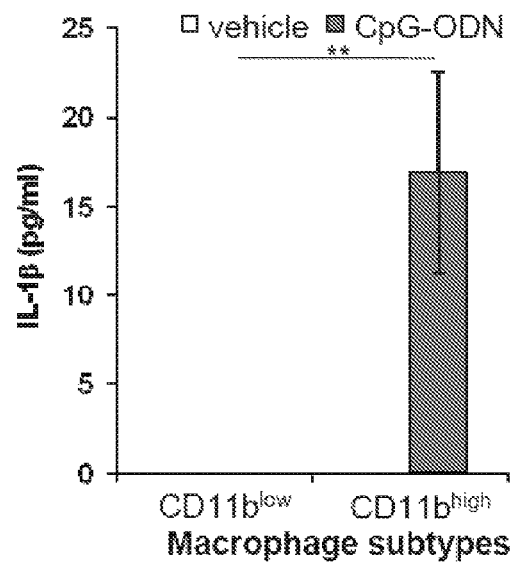

Responsiveness of $CD11b^{high}$ Macrophages to TLR (Toll-Like Receptors) Ligands Sorted macrophages were activated with LPS, and the secretion levels of TNF-α, IL-β, IL-10, and TGFβ by $CD11b^{high}$ and $CD11b^{low}$ macrophages were determined. The results are presented in FIGS. 3A-3D. $CD11b^{high}$ macrophages were found to secrete twice as much TNF-α as $CD11b^{low}$ macrophages in the absence of LPS. Stimulation with LPS at 500 ng/mL resulted in a significantly elevated and maximal secretion of TNF-α by $CD11b^{high}$ macrophages, whereas $CD11b^{low}$ macrophages did not increase their TNF-α secretion. Similar results were obtained when the secretion of the pro-inflammatory cytokines and chemokines IL-1β, CCL2, CCL3 and CCL5 was determined (FIGS. 3B, 3E-3G). The secretion of IL-10, an anti-inflammatory cytokine, was also increased in $CD11b^{high}$ macrophages stimulated with LPS (FIG. 3C). The secretion of the resolution-promoting cytokine TGFα was higher in $CD11b^{low}$ macrophages, but did not increase following activation with LPS (FIG. 3D).

In addition, $CD11b^{low}$ and $CD11b^{high}$ macrophages were stimulated with the TLR3 and TLR9 ligands poly (I:C) and CpG-oligodeoxynucleotides (CpG-ODN), respectively, and the secretion of TNF-α and IL-β was determined (FIG. 4). The results indicate that both TNF-α and IL-β secretion were increased following exposure to poly (I:C) and CpG-ODN of CD11b$^{high}$ macrophages, whereas the secretion of these cytokines by CD11b$^{low}$ macrophages treated in the same manner was significantly lower. No significant reduction in the expression of TLR3, 4 and 9 was found in CD11b$^{low}$ macrophages, in comparison to their CD11b$^{high}$ counterparts. Thus, CD11b$^{low}$ macrophages are poorer responders to different TLR ligands in terms of cytokine and chemokine secretion, and therefore may be considered immune-silent.

Example 4

The Phagocytic Capacity of CD11b$^{low}$ and CD11b$^{high}$ Macrophages

Figure 5A:
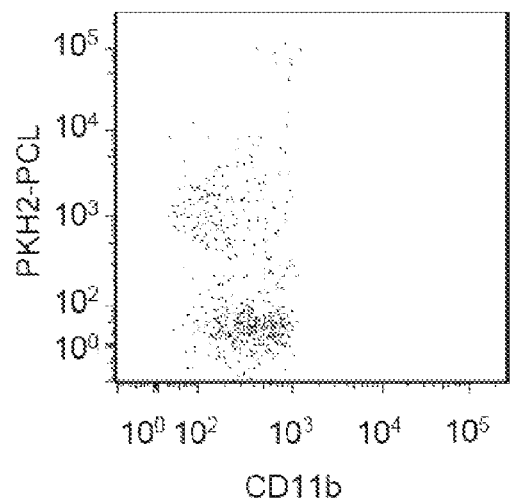
FIGS. 5A-5C show that CD11b$^{low}$ macrophages are satiated. PKH2-PCL-green was injected intraperitoneally (i.p.) to mice 48 hrs post peritonitis initiation. After 4 hrs, the peritoneal cells were recovered, immune-stained for F4/80 and CD11b and analyzed using FACSCalibur. Results are representative dot plot for CD11b$^{low}$ (A) and CD11b$^{high}$ macrophages (B), or mean fluorescence intensity (MFI) values±SE of 5 experiments (C). Significant differences by Student's t test between CD11b$^{high}$ and CD11b$^{low}$ macrophages (*** P value<0.001) are indicated.
Figure 5B:
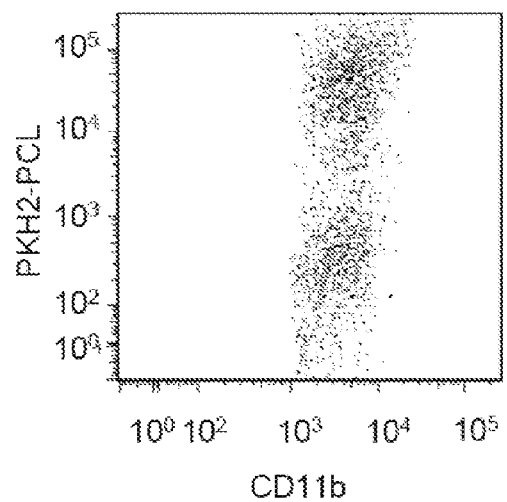
Figure 5C:
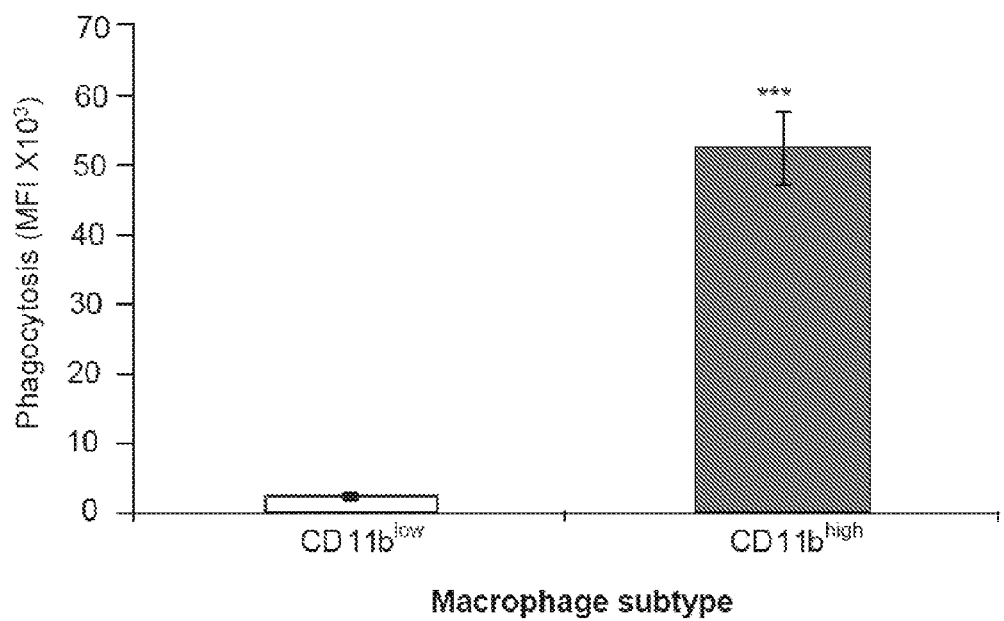

To determine whether CD11b$^{low}$ and CD11b$^{high}$ macrophages differ in their ability to phagocytose external particles, the phagocyte-specific dye PKH2-PCL green was injected intraperitoneally (i.p.) to mice undergoing peritonitis for 48 and 4 h later the peritoneal cells were recovered, immunostained, and analyzed for PKH2-PCL acquisition. The results are shown in FIG. 5. Most CD11b$^{low}$ macrophages did not acquire PKH2-PCL (FIG. 5A), whereas the majority of CD11b$^{high}$ macrophages acquired higher amounts of PKH2-PCL (FIG. 5B). As a result, the mean fluorescence intensity (MFI) of PKH2-PC was 410-fold higher in CD11b$^{high}$ macrophages (FIG. 5C).

Thus, CD11b$^{low}$ macrophages may be considered "satiated", meaning that they lost their phagocytic potential upon meeting the apoptotic PMN engulfment threshold and reducing their CD11b expression.

Example 5

Migration of CD11b$^{low}$ Macrophages to Lymphoid Organs

Figure 6A:
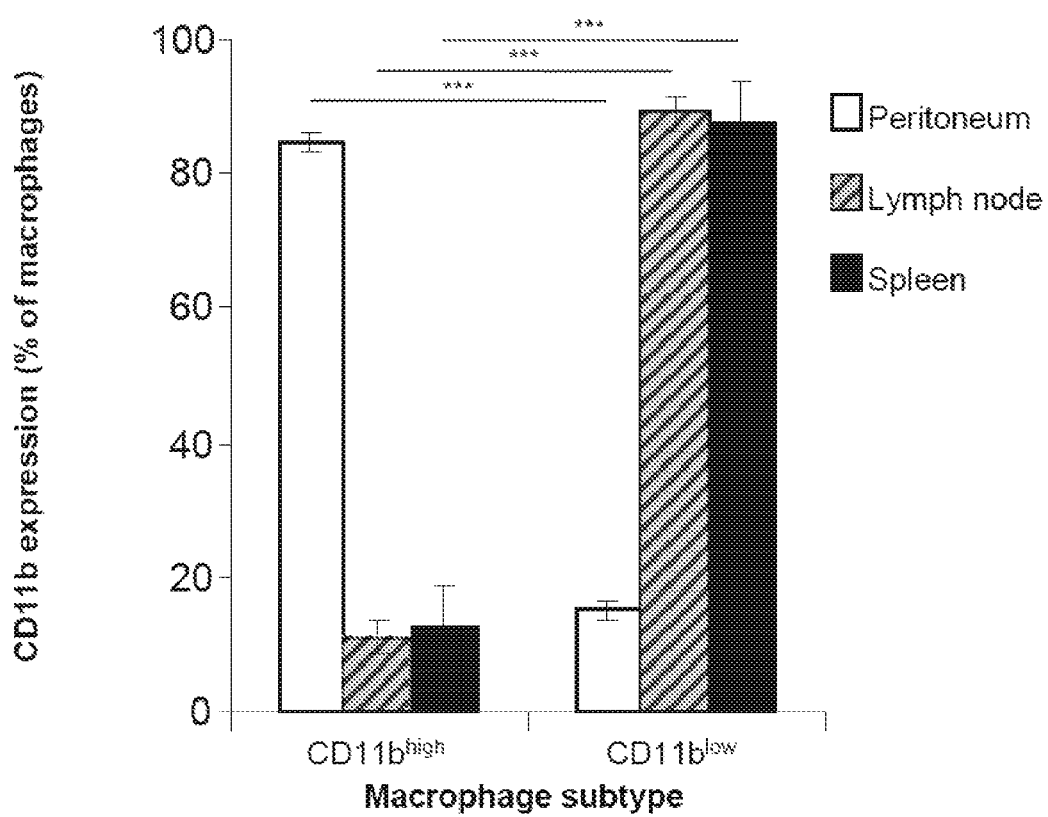
FIGS. 6A-6B show that CD11b$^{low}$ macrophages are prone to migrate to lymphoid organs. (A) Cells were recovered from the peritoneum (white), inguinal lymph node (LN, striped) and spleen (black) of mice undergoing peritonitis for 66 hrs. The cells were stained as above and CD11b expression on macrophages was determined by flow cytometry. (B) Macrophages were recovered from peritoneal exudates 48 hrs post peritonitis initiation, labeled with CFSE, and transferred to recipient mice undergoing peritonitis for the same period. After 18 hrs, the cells from the peritoneum (white), inguinal LN (striped, and spleen (black) were recovered and the expression of CD11b on transferred macrophages was determined as above. Results presented are mean±SE from three experiments, 5 mice per experiment. Significant differences by Student's t test between CD11b$^{high}$ and CD11b$^{low}$ macrophages (* P value<0.05,  P value<0.005, * P value<0.001) are indicated.
Figure 6B:
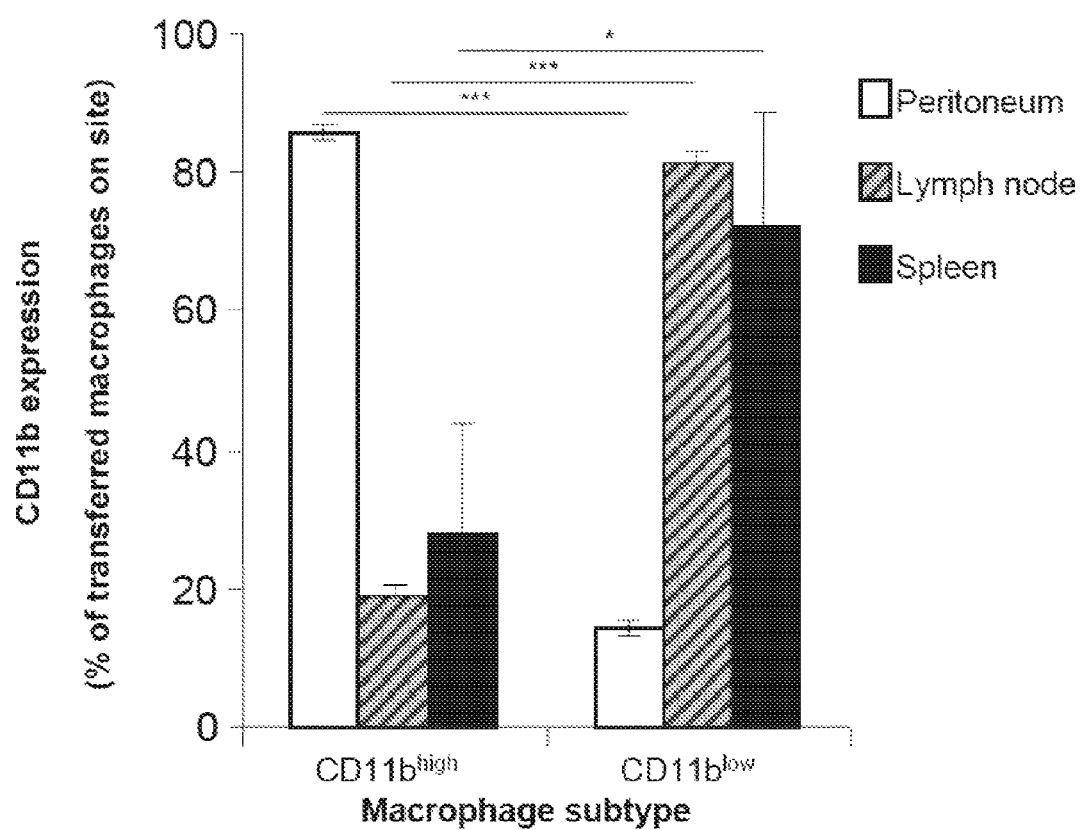

To determine whether CD11b$^{low}$ macrophages are prone to depart resolving inflammation sites and emigrate to lymphoid organs, the relative distribution of CD11b$^{high}$ and CD11b$^{low}$ macrophages 66 h post-peritonitis initiation was determined at the peritoneum, inguinal LN, and spleen. The results (FIG. 6A) indicate that CD11b$^{high}$ macrophages are the predominant macrophage subtype in the peritoneum during late resolution, whereas, at the same time CD11b$^{low}$ macrophages are the predominant macrophage subtype at the LN and spleen. To examine whether CD11b$^{low}$ macrophages at the LN and spleen originated in the peritoneum, adoptive transfer experiments were performed in which peritoneal macrophages were isolated and labeled fluorescently, and then transferred to the peritoneum of mice undergoing peritonitis at the same period (48 h). The results (FIG. 6B) indicate that, 18 h after transfer, the distribution of labeled CD11b$^{high}$ and CD11b$^{low}$ macrophages at the peritoneum, inguinal LN and spleen was similar to the distribution of unlabeled macrophages.

Example 6

Ex-Vivo Generation of Macrophages Expressing Low Levels of CD11b

Figure 7A:
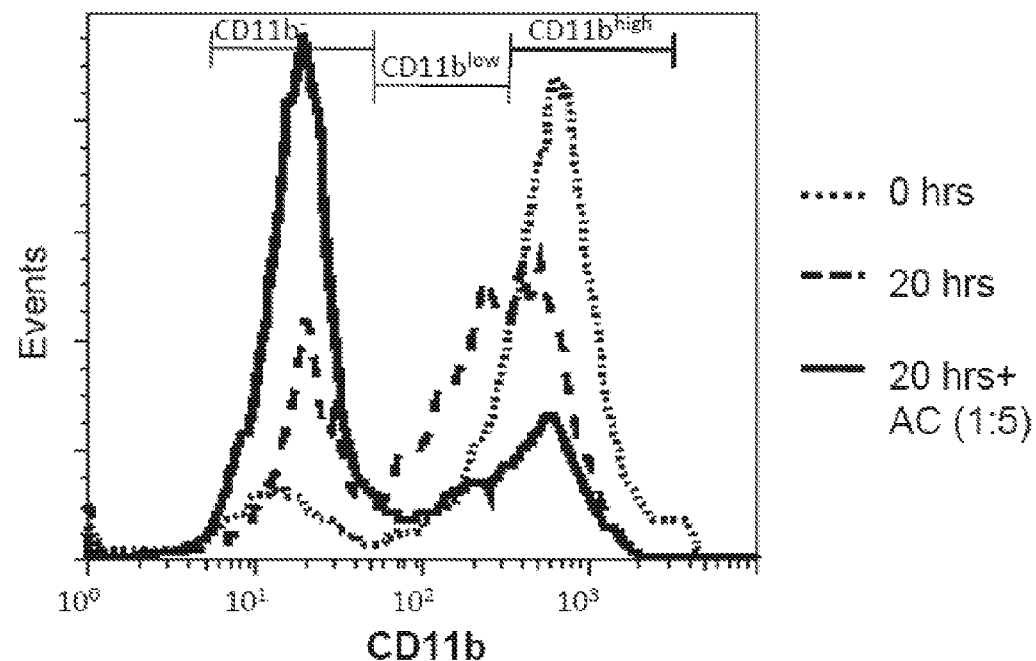
FIGS. 7A-7D show that interaction with apoptotic leukocytes converts CD11b$^{high}$ macrophages to CD11b$^{low}$ macrophages. Sorted CD11b$^{high}$ (A) or CD11b$^{low}$ (B) macrophages were immunostained for CD11b immediately (A-B, dotted line), or after incubation for 20 hrs without cells (A-B, dashed line) or with apoptotic Jurkat cells (1:5 ratio; A-B, solid line). Then the unbound apoptotic cells were washed and the macrophages were recovered and immunostained for CD11b expression on their surface. Results are representative (A, B; depicted macrophage populations indicated) or average MFI values±SE (C) of 3 experiments; white bars: incubation w/o cells, black bars: incubation with apoptotic cells). Significant differences by Student's t test between CD11b$^{high}$ and CD11b$^{low}$ macrophages (* P value<0.05,  P value<0.005, * P value<0.001) are indicated. (D). Peritoneal macrophages were recovered 66 hrs post peritonitis initiation and incubated with apoptotic Jurkat cells (+) or without cells (−), as indicated. After 20 hrs the macrophages were recovered and lysed. The protein extracts were run by SDS-PAGE and analyzed by Western blot for CD11b, arginase-1, 12/15-LO, actin and tubulin as loading control. Results are a representative set of blots from 3 experiments.
Figure 7B:
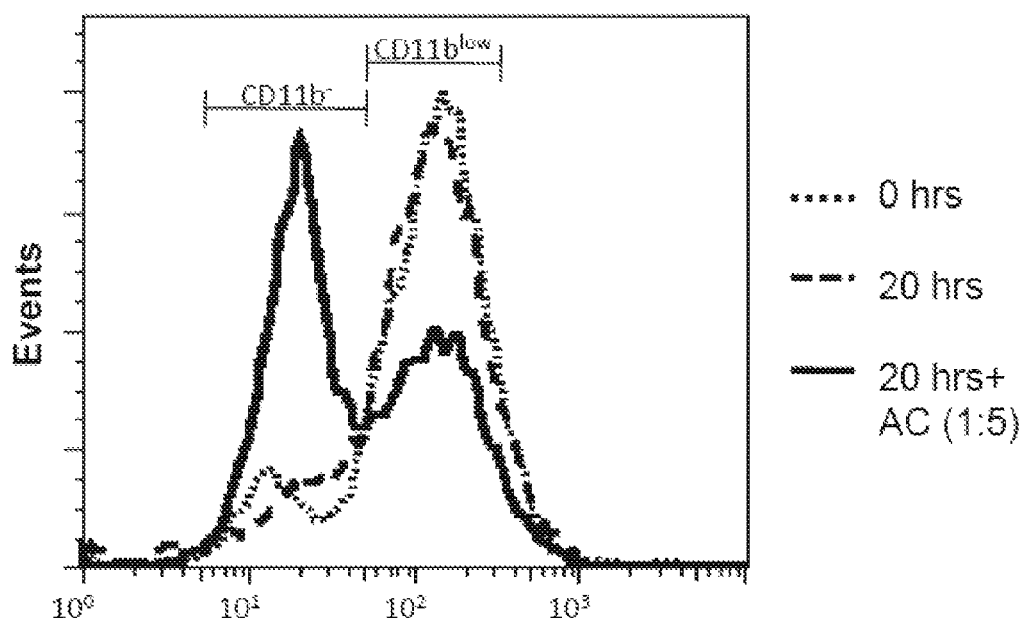
Figure 7C:
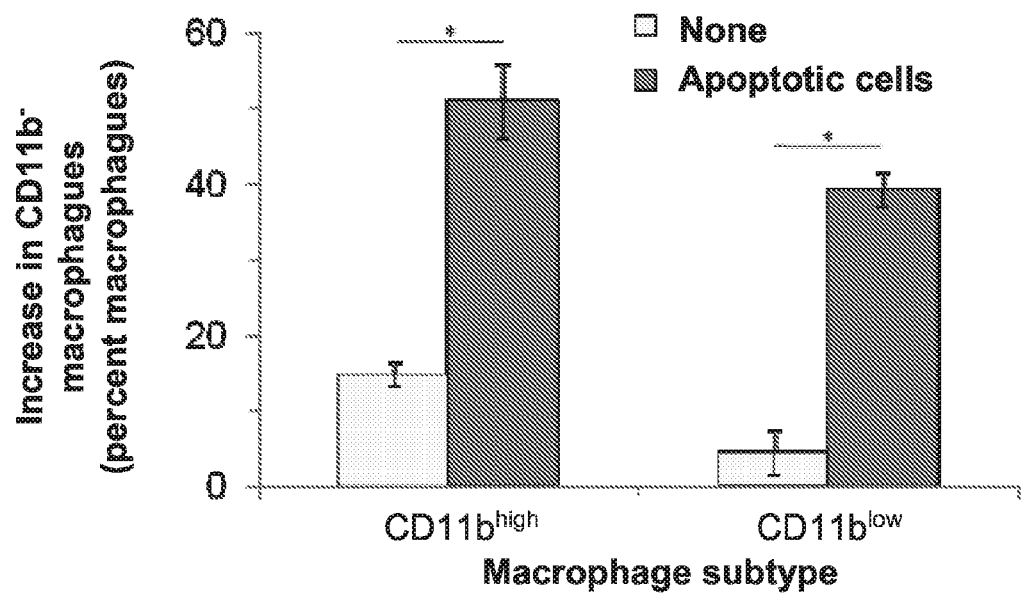

Sorted CD11b$^{high}$ and CD11b$^{low}$ macrophages were incubated with or without apoptotic Jurkat cells and the changes in surface expression of CD11b were determined. The results (FIGS. 7A, B) indicate that CD11b expression on the surface of both CD11b$^{high}$ and CD11b$^{low}$ macrophages was significantly reduced, following their incubation with apoptotic cells, and some of the macrophages had even lower expression levels compared to the level of expression found for CD11b$^{low}$ macrophages recovered from peritoneal exudates. Therefore the ex vivo-generated population of macrophages expressing low levels of CD11b may be comprised from both CD11b$^{low}$ and CD11b$^-$ macrophages (FIG. 7C). No significant reduction in surface expression of F4/80 or of CD11b was observed following macrophage incubation with latex beads (LB) or IgG-opsonized LB (data not shown). The impact of apoptotic cells was partially mimicked by CD11b ligation with monoclonal antibodies, which resulted in a decrease in CD11b, but not of F4/80, surface expression, thus suggesting CD11b is involved in the signaling cascade that leads to its own down-regulation. Notably, CD206 and CD163 surface expression was not modulated by AC ex vivo, but was reduced by anti-CD11b antibodies. Exposure to zymosan A, TGFP, or live cells did not result in a significant reduction in the surface expression of CD11b (data now shown).

The reduction in macrophage CD11b expression ex vivo appears to be specific for interaction with apoptotic cells, and could not be achieved by treatment with other phagocytic targets, prototypic-activating bacterial moieties, or pro-resolving cytokines, and is not due to the cell type of the apoptotic cells.

Figure 7D:
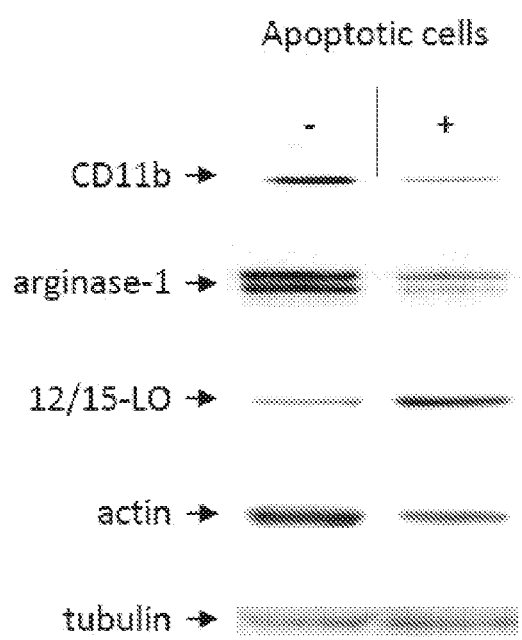

To determine whether macrophage interaction with apoptotic cells also triggers the major differences in protein expression distinguishing CD11b$^{high}$ and CD11b$^{low}$ macrophages that are shown in FIG. 1, peritoneal macrophages were incubated with apoptotic cells and changes in the cytoplasmic content of CD11b, arginase-1, 12/15-LO and actin were determined. The results (FIG. 7D) show that macrophages incubated with apoptotic cells expressed reduced levels of CD11b and arginase-1, and increased levels of 12/15-LO. The levels of detergent-soluble actin in macrophages were also reduced, following incubation with apoptotic cells. These findings are consistent with the findings in FIG. 1 that show reduced actin levels in lysates of CD11b$^{low}$ macrophages, in comparison to their CD11b$^{high}$ counterparts.

Ex vivo exposure of macrophages to senescent neutrophils, but not to latex beads (LB) or IgG-opsonized LB, resulted in a significant reduction in CD11b and arginase-1 expression, whereas 12/15-LO expression was increased in this setting by all phagocytic targets. These results indicate that interaction with apoptotic cells is sufficient to drive the conversion of CD11b$^{high}$ to CD11b$^{low}$ macrophages.

Example 7

RvD1, RvE1, and Dex Reduce the PMN Engulfment Threshold Required for Macrophage Immune-Silencing Resolvins are resolution-phase-generated mediators derived from Ω-3 polyunsaturated fatty acids; they were found to promote resolution by acting on PMN and macrophages. Similar properties were attributed to glucocorticoids, such as dexamethasone (Dex), that inhibit leukocyte infiltration to inflammation sites and promote the clearance of apoptotic PMN by macrophages. To determine whether pro-resolving mediators regulate emergence of CD11b$^{low}$ macrophages and thereby promote resolution, RvD1, RvE1, or Dex were introduced into peritonitis-affected mice, and the recovered leukocytes were collected and analyzed for macrophage and neutrophil numbers, macrophage CD11b expression, engulfment of PMN, and responsiveness to LPS. The results are presented in FIG. 8 of Schif-Zuck et al., 2011, which is incorporated herein by reference. These results indicate that RvD1, RvE1 and Dex induced a reduction in neutrophil numbers, whereas RvD1 and Dex, but not RvE1 also reduced the number of macrophages in peritoneal cavities. In addition, RvD1, RvE1 and Dex enhanced the appearance of CD11b$^{low}$ macrophages (32.8±8.8%, 46.2±1.8%, and 39.9±4.6% increases over vehicle treatment, for RvD1, RvE1, and Dex, respectively) in peritoneal exudates. RvD1 and RvE1, but not Dex, also reduced CD11b expression on CD11b$^{high}$ macrophages. To determine whether RvD1, RvE1, and Dex regulate apoptotic PMN engulfment by macrophages during resolution, exudate cells were enumerated for PMN engulfment and analyzed as in FIG. 2. The results indicate that RvD1 and, to a greater extent, RvE1 and Dex, reduced the numbers of apoptotic PMN engulfed by macrophages present in the peritoneum. A detailed analysis of engulfment according to thresholds indicated that RvE1 and Dex, but not RvD1, induced the appearance in the peritoneum of low-engulfing macrophages, designate "inexperienced" since they phagocytosed less than 2 Neutrophil engulfed per macrophage (N/M).

To validate the improvement in immune-silencing of macrophages that followed treatment with RvD1, RvE1 and Dex, macrophages were activated with LPS, and cytokine secretion was determined. The results indicate that RvD1 and RvE1, and, to a lesser extent, Dex, inhibited the secretion of TNFα from unstimulated and LPS-stimulated macrophages. A similar response was observed with RvD1, RvE1 and Dex when IL-1β secretion from LPS-stimulated macrophages was determined. The secretion of IL-10, a pro-resolving cytokine generated following the ingestion of apoptotic cells, was up-regulated by each of the pro-resolving mediators, in unstimulated and LPS-stimulated macrophages. Thus, treatment with RvD1, RvE1, and Dex, promoted macrophage immune-silencing, as well as the secretion of pro-resolving cytokines from these cells.

Figure 8A:
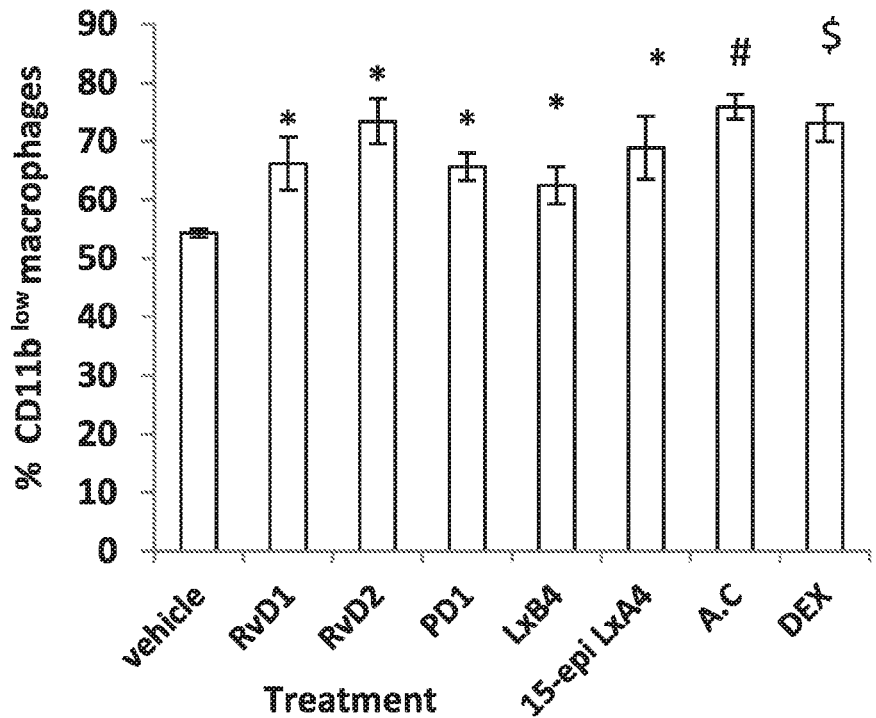
FIGS. 8A-8B show promotion of macrophage switch to the CD11b$^{low}$ phenotype by pro-resolving lipid mediators. Macrophages were recovered from peritoneal exudates 72 hrs post peritonitis initiation and incubated overnight with vehicle, RvD1, RvD2, PD1, LXB$_4$, or 15-epi-LXA$_4$, (all at 50 nM), apoptotic cells (M/N ratio of 1:5), or Dex (25 μg/ml dexamethasone). Then, the cells were stained for CD11b and analyzed by flow cytometry, and the percentage of CD11b$^{low}$ (A) and CD11b$^{high}$ (B) macrophages was determined. Results are mean±SE of two experiments (n=2). #P<0.005, $ P<0.01, * P<0.05 compared to vehicle.
Figure 8B:
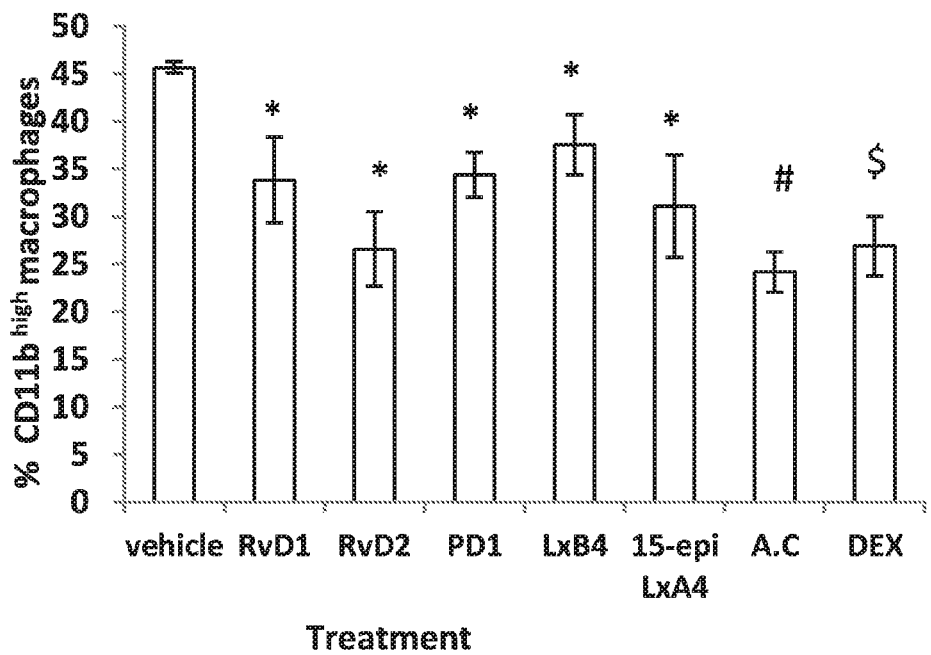

FIG. 8 show promotion of macrophage switch to the CD11b$^{low}$ phenotype by pro-resolving lipid mediators. Macrophages were recovered from peritoneal exudates 72 hrs post peritonitis initiation and incubated overnight with vehicle (RPMI 10% FBS+0.05% ethanol), RvD1, RvD2, PD1, LXB$_4$, or 15-epi-LXA$_4$, (all at 50 nM), apoptotic cells (M/N ratio of 1:5), or Dex (25 µg/ml). Then, the cells were stained for CD11b and analyzed by flow cytometry, and the percentage of CD11b$^{low}$ (A) and CD11b$^{high}$ (B) macrophages was determined. Results are mean±SE of two experiments (n=2). #P<0.005, $ P<0.01, * P<0.05 compared to vehicle.

Example 8

Ex Vivo Treatment with Pro-Resolving Lipid Mediators Promotes Macrophage Switch to the CD1b$^{low}$ Phenotype Macrophages were recovered from peritoneal exudates 72 hrs post peritonitis initiation and incubated overnight with either RPMI 10% FBS+0.05% ethanol, the resolvins RvD1 or RvD2, cell death protein PD1 or lipoxins LXB$_4$, or 15-epi-LXA$_4$, (all at 50 nM), apoptotic cells (M/N ratio of 1:5), or Dex (25 µg/ml). After 20 hours, the cells were stained for CD11b and analyzed by flow cytometry. As can be seen from FIG. 8, all of the treatments significantly elevated the percentage of CD11b$^{low}$ macrophages (8A) and reduced the percentage of CD11b$^{high}$ (8B) macrophages.

Example 9

Figure 10A:
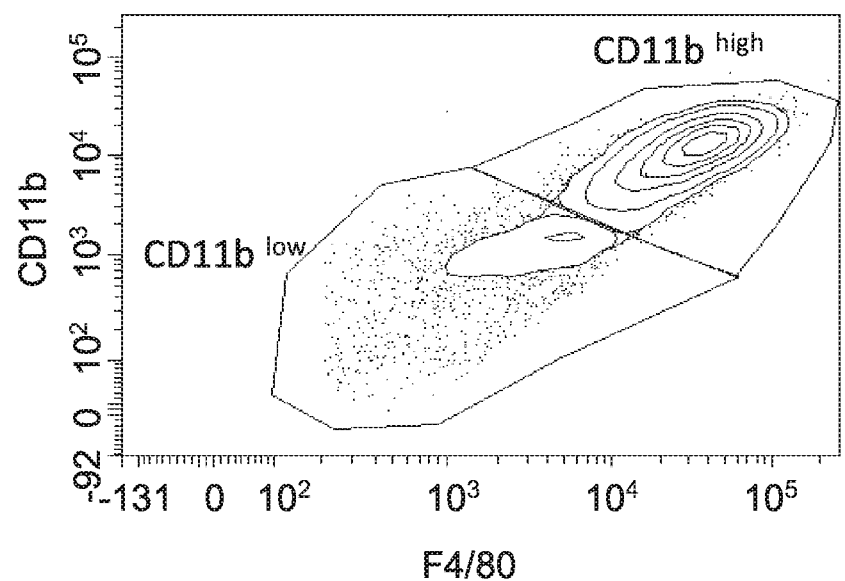
FIGS. 10A-10D show conversion of CD11b$^{high}$ macrophages to CD11b$^{high}$ macrophages to CD11b$^{low}$ macrophages upon their incubation with apoptotic cells at a ratio of Mφ to apoptotic cells (AC) of 1:5. A-D show FACS analysis of CD11b$^{high}$ macrophages either untreated (A) or incubated with apoptotic cells (AC) overnight (O.N.) (B-D). A. Characterization of untreated CD11b$^{high}$ macrophages (Mφ) stained positively for F4/80, for CD11b expression levels after O.N incubation. B. Histogram of macrophages identified by staining positively for F4/80, after incubation with AC at a ratio of 1:5. C. Characterization of Mφ stained positively for F4/80, for CD11b levels after O.N incubation with AC cells at a ratio of 1:5. D. The percentage of CD11b (black bars) and CD11b$^{low}$ (white bars) macrophages of untreated Mφ or Mφ incubated with AC at a ratio of 1:5 (Mφ+AC(1:5)). Representative result (n=3).
Figure 10B:
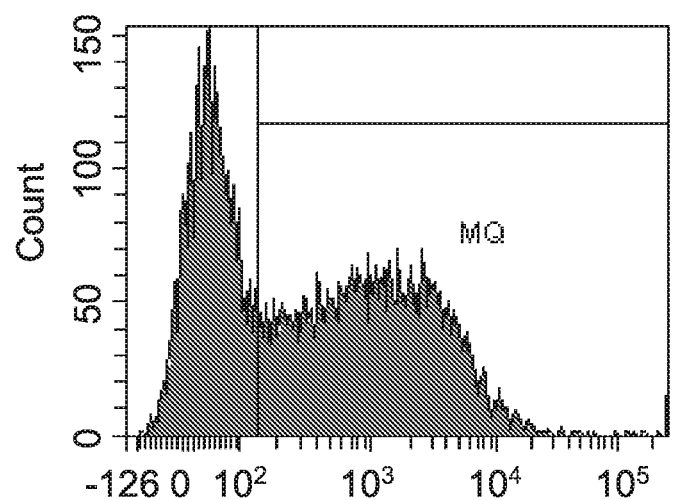
Figure 10C:
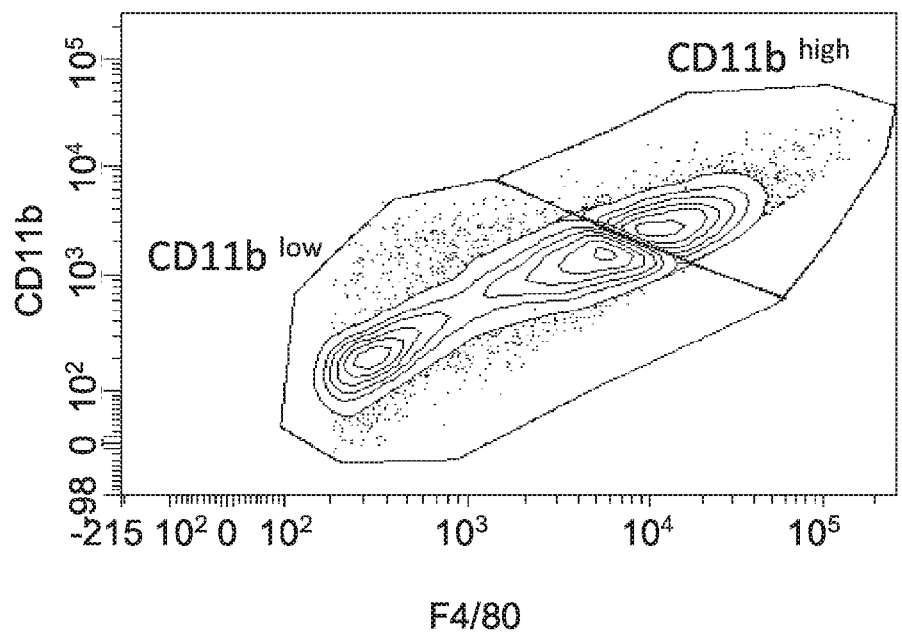
Figure 10D:
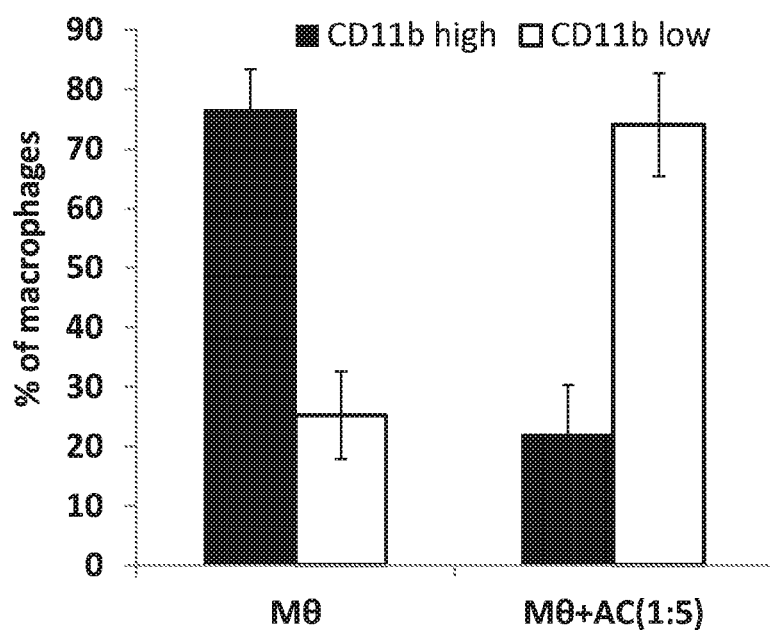
Figure 11A:
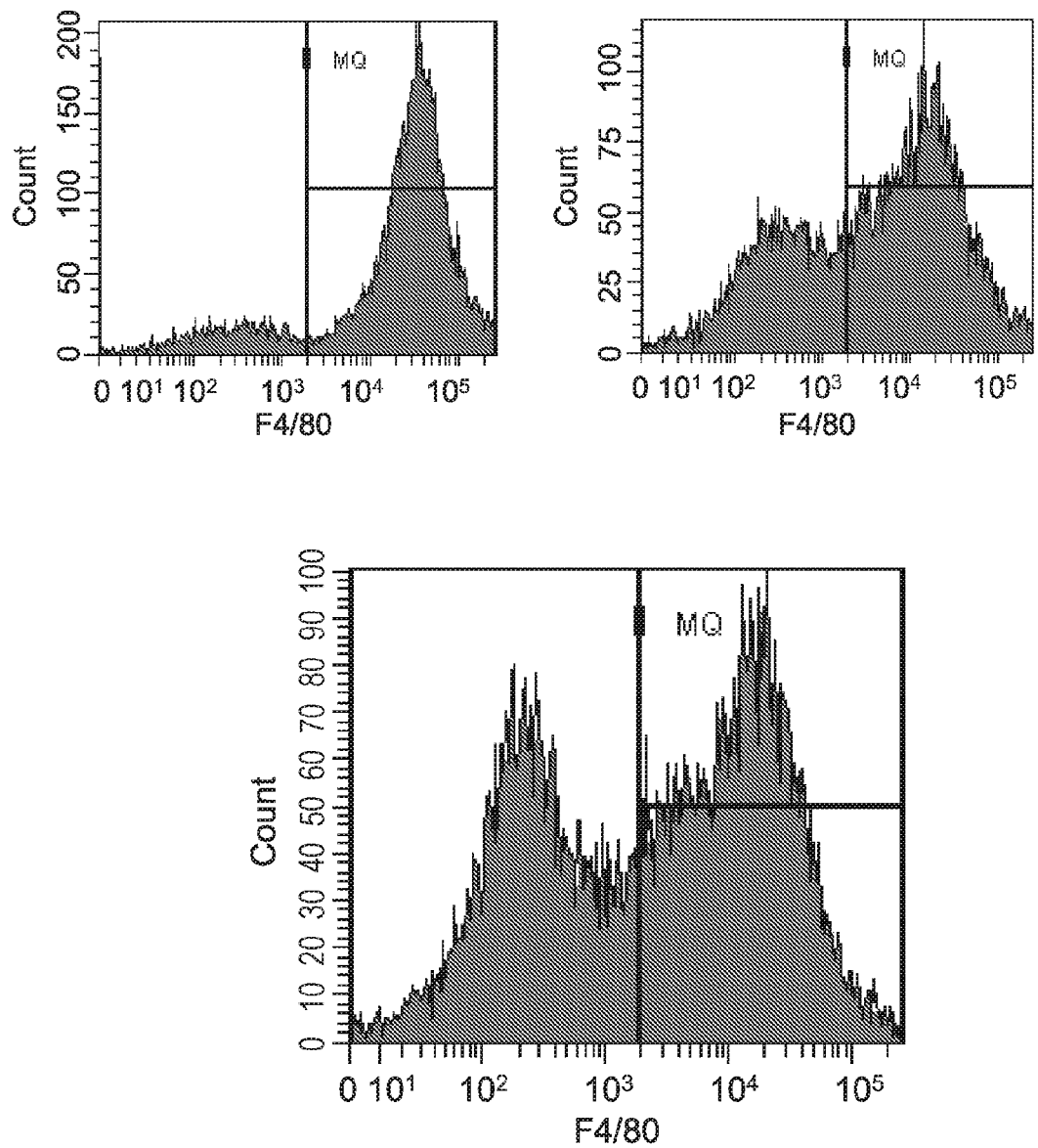
FIGS. 11A-11D show conversion of CD11b$^{high}$ macrophages to CD11b$^{low}$ macrophages upon their incubation with apoptotic cells at a ratio of Mφ to apoptotic cells (AC) of 1:1 or 1:2. A-D show FACS analysis of CD11b$^{high}$ macrophages either untreated or incubated O.N with apoptotic cells (AC). A. Histogram of macrophages identified by staining positively for F4/80, either untreated (top left panel) or incubated with AC at a ratio of 1:1 or 1:2 (top right panel and bottom panel, respectively). B. Characterization of F4/80 positive macrophages either untreated (top panel) or incubated with AC at a ratio of 1:1 or 1:2 (middle panel and bottom panel, respectively), for CD11b expression levels. C. The percentage of CD11b$^{high}$ (black bars) and CD11b$^{low}$ (white bars) macrophages of untreated Mφ (left pair) or Mφ incubated with AC at ratios of 1:1 or 1:2 (middle bar and right bar, respectively). Representative result (n=3). D. Percentage of the residual AC which did not undergo engulfment by CD11b$^{high}$ macrophages when incubated with AC at ratio of 1:1, 1:2 and 1:5 (from left to right).
Figure 11B:
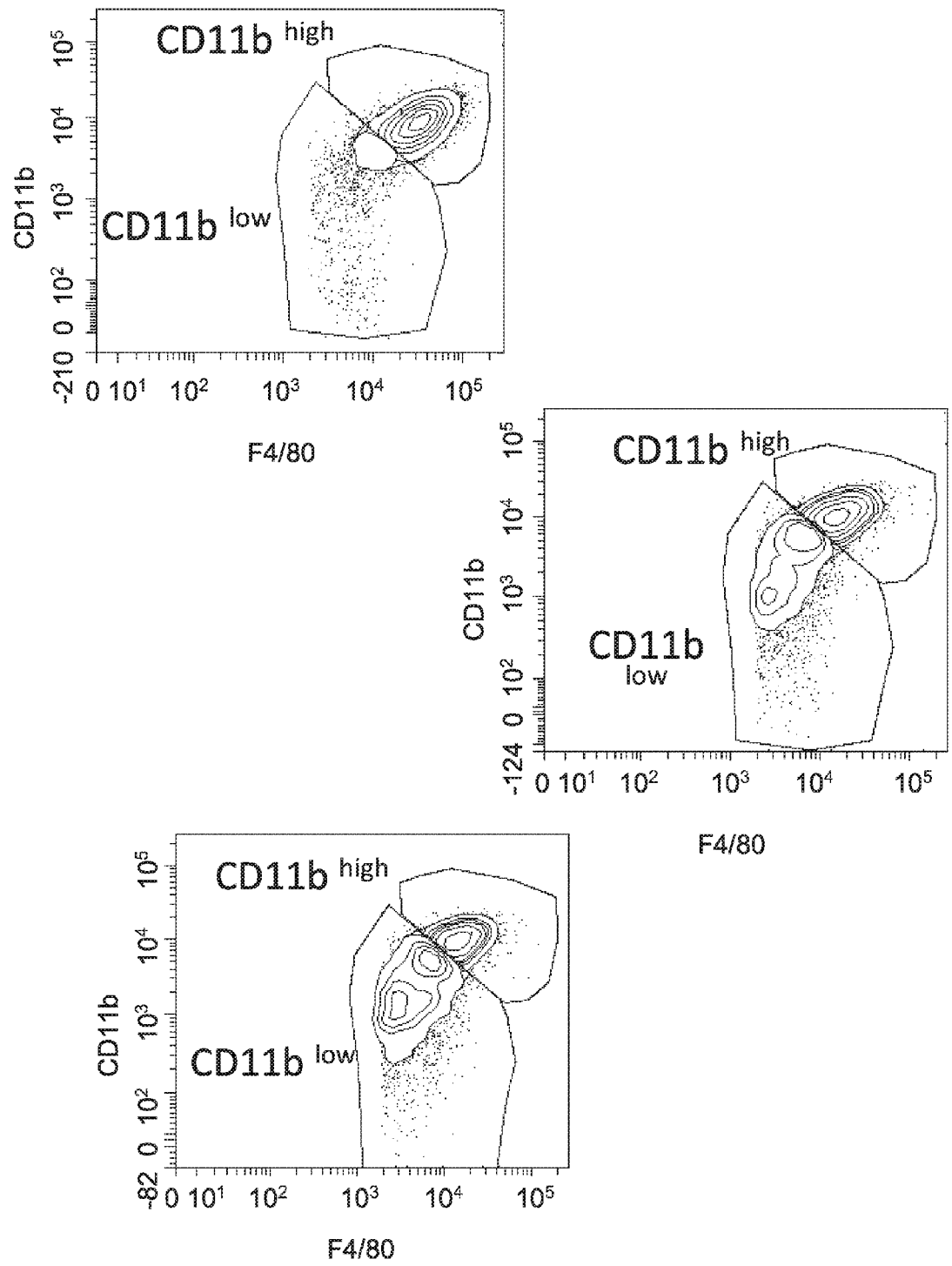
Figure 11C:
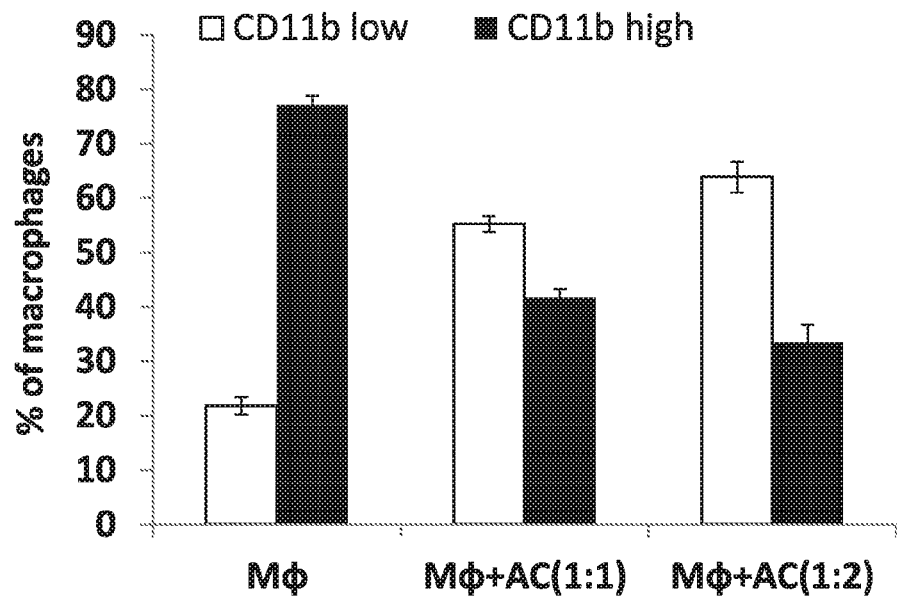
Figure 11D:
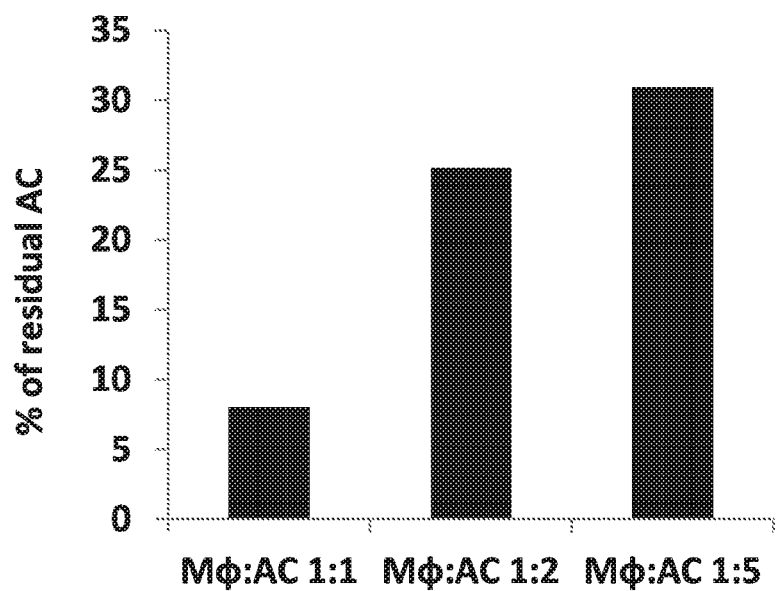

Ex-Vivo Generation of Secreted Factors of Pro-Resolving CD11b$^{low}$ Macrophages Conditioned media of enriched CD11b$^{high}$ macrophages (CM-Mck) and of ex-vivo generated pro-resolving CD11b$^{low}$ macrophages (CM-Mres) was collected in order to test their impact on the formation of a fibrotic ECM by myofibroblasts and the transition from tumor dormancy to metastatic growth as detailed below. To this end peritonitis was induced and 66 hours later peritoneal exudates were collected and the percentage of macrophages was determined in peritoneal exudates, based on their size and granularity (FIG. 9A, see gated area and red arrow) and positive staining for F4/80 (FIG. 9B). The majority of the cells (55% of the exudates) were macrophages (FIG. 9C) as determined by FACS analysis (FIGS. 9A and B). Furthermore, 66% of the macrophages expressed high levels of CD11b and 34% expressed low levels of CD11b (FIG. 9D-E) indicating that resolution was already initiated in vivo. Next, CD11b$^{high}$ macrophages were collected and were either untreated (FIG. 10A) or treated with apoptotic Jurkat cells (a common apoptotic leukocyte target for macrophages in experimental procedures; as described in Schif-Zuck et al., 2011, with some modifications). Originally, CD11b$^{high}$ macrophages were incubated with apoptotic Jurkat cells at a ratio of 1:5 respectively (FIG. 10B) resulting in 80% conversion of CD11b$^{high}$ macrophages to CD11b$^{low}$ macrophages compared to untreated macrophages where only 25% of CD11b$^{high}$ macrophages were converted to CD11b$^{low}$ macrophages, as determined by surface expression of CD11b by FACS analysis and as illustrated in FIG. 10C-D. However, 30% of the apoptotic cells (AC) were not engulfed by CD11b$^{high}$ macrophages (FIG. 11D). Given that we planned on using the conditioned media of the untreated and treated macrophages it was essential to reduce the presence of non-engulfed AC cells to avoid potential residual effect of the AC in the conditioned media. Hence, we tested whether we can successfully generate ex-vivo the CD11b$^{low}$ macrophages by incubating CD11b$^{high}$ macrophages with AC at a ratio of 1:2 and 1:1 respectively. Importantly, after incubating the CD11b$^{high}$ macrophages with AC we collected the conditioned media (that will be utilized for our experiments as will be detailed below), and characterized the macrophages according to their staining for F4/80 (as illustrated in FIG. 11A) and CD11b expression levels (as illustrated in FIG. 11B). Indeed, we found that the majority of the CD11b$^{high}$ macrophages converted to CD11b$^{low}$ macrophages upon incubation with lower amounts of AC. CD11b$^{high}$ macrophages to AC ratios of 1:2 and 1:1 yielded conversion of 60% and 55% of CD11b$^{high}$ macrophages to CD11b$^{low}$ macrophages respectively compared to untreated macrophages where only 20% of CD11b$^{high}$ macrophages were converted to CD11b$^{low}$ macrophages (FIG. 11C). Importantly, only 8% of the AC remained after incubation of CD11b$^{high}$ macrophages with AC at 1:1 ratio, compared to 25% at 1:2 ratios (FIG. 11D).

Example 10

CM-Mres Prevents Fibroblasts Differentiation to Myofibroblasts in 2 Dimensional Cultures We next determined whether conditioned media recovered during the conversion of CD11b$^{high}$ macrophages to CD11b$^{low}$ macrophages (CM-Mres) (as described in Example 9) was able to inhibit the differentiation of fibroblasts to myofibroblasts. In order to address this question we tested proliferation of fibroblasts, their expression of α-SMA and expression and deposition of Type I collagen (Col-I) upon treatment with CM-Mres.

Figure 12:
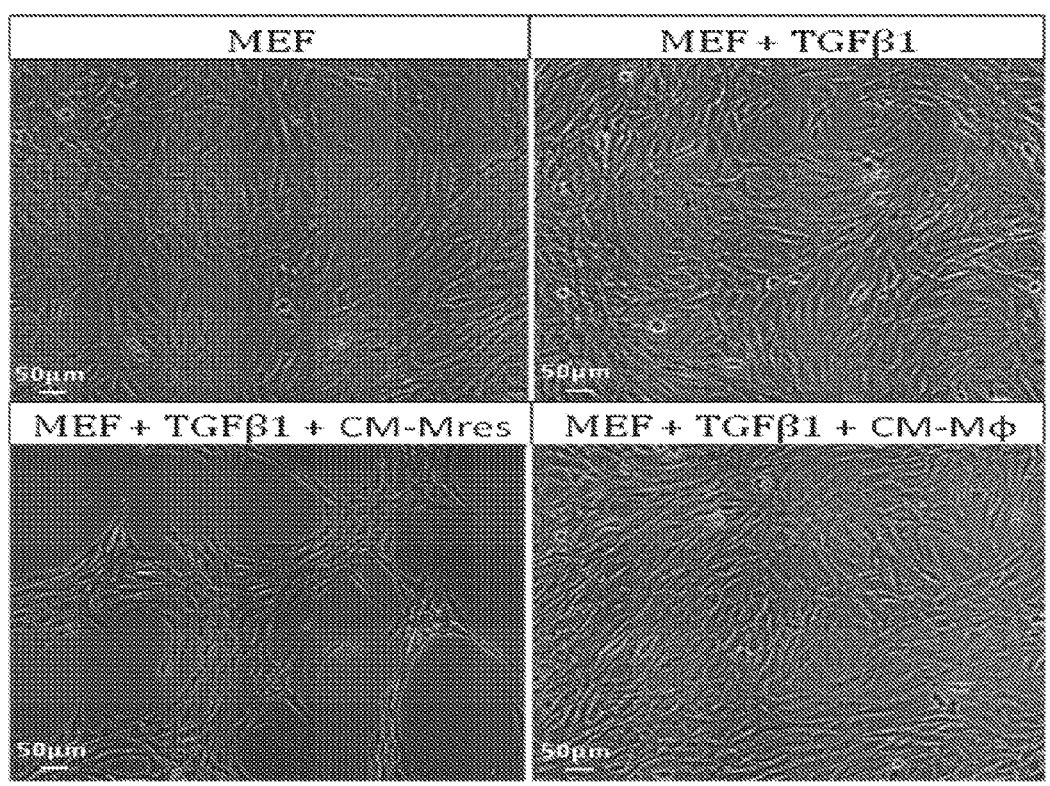
FIG. 12 shows reduction in MEF number upon incubation with conditioned media of enriched CD11b$^{low}$ macrophages (CM-Mres) with TGFβ1 (panel at the lower left). Representative bright field microscopy images of MEF grown on coaster 6 plate. Magnification ×20. Bars equal 50 μm: upper panels, left: MEF alone; right: MEF with TGFβ1; lower panels, left: MEF with TGFβ1 and CM-Mres; right: MEF with TGFβ1 and conditioned media of enriched CD11b$^{high}$ macrophages (CM-Mck).

Initially, we carried out a qualitative experiment to determine the growth of fibroblasts. To this end mouse embryonic fibroblasts (MEFs) were induced to differentiate to myofibroblasts by treating the cells with 1 ng/ml TGFβ1 for 72 hours. To test the impact of the conditioned media on the activation of MEFs we carried out the following: 1 hour prior to adding TGFβ1, the MEFs were either untreated or treated with either condition media of CD11b$^{high}$-enriched macrophages (CM-Mφ)) or with CM-Mres for 72 hours. Our results demonstrate that fewer MEFs were present in plates treated with CM-Mres and TGFβ1, compared to untreated MEF or to MEF treated with either CM-Mφ and TGFβ1 or with TGFβ1 alone (FIG. 12).

Example 11

MEFs Treated with CM-Mres are Cell cycle Arrested

We further studied whether reduction in the number of MEFs that were treated with TGFβ1+CM-Mres was due to inhibition of proliferation. To this end condition media from either cultured residual AC (CM-AC), CM-Mφ or CM-Mres was overlaid on starved MEFs cultured on 96 well plates 1 hour prior to TGFβ1 treatment. Proliferation of the cells was monitored 24, 48 and 72 hours after addition of TGFβ1.

Figure 13A:
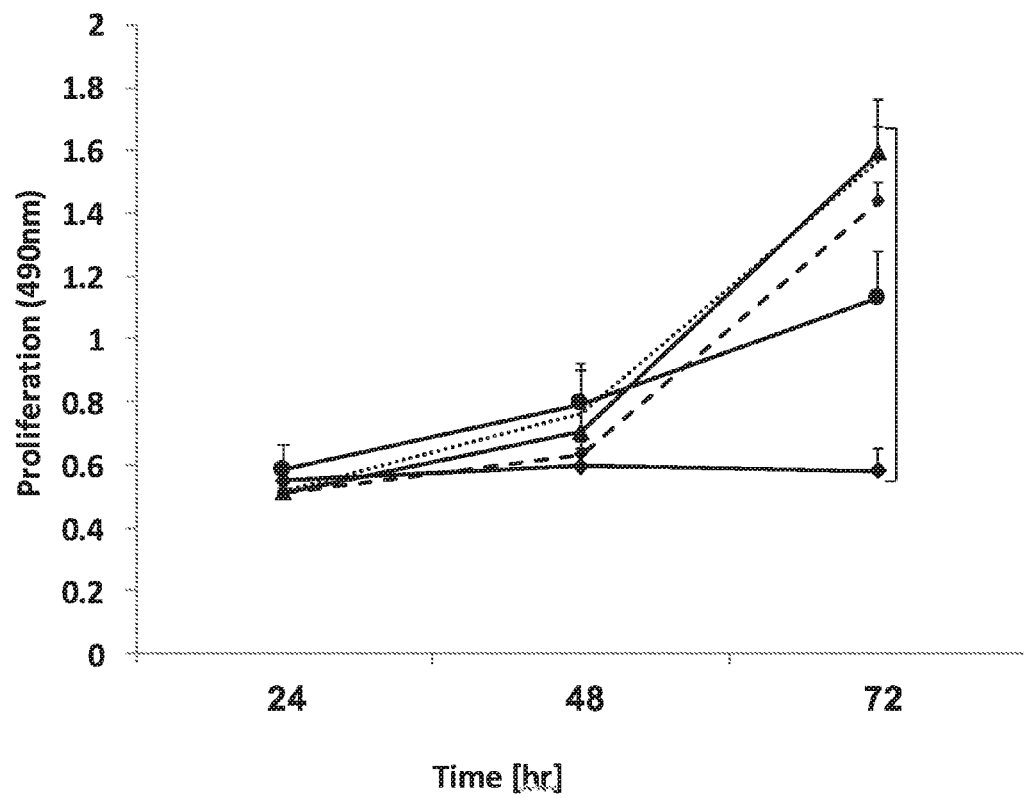
FIGS. 13A-13B show that MEFs treated with CM-Mres are cell cycle arrested and not apoptotic. A. Proliferation of MEF cells either untreated (diamonds on dashed line) or treated with TGFβ1 alone (dotted line), or with TGFβ1 in the presence of conditioned medium from either CD11b$^{high}$-enriched (CM-Mφ, triangles), CD11b$^{low}$-enriched (CM-Mres, diamonds on solid line) or apoptotic cells (CM-AC, circles). (n=5). B. Quantification of the percentage of MEFs undergoing apoptosis. Percentage of apoptotic cells from total cell number was determined by TUNEL assay (n=3, no significance). From left to right: MEF untreated, or treated with 1 ng/ml TGFβ1, TGFβ1+CM-Mres, or 1.5 μg/ml staurosporine (STS) (positive control).

Our results demonstrate that TGFβ1 promotes the proliferation of MEF as expected in a time dependent manner. Furthermore CM-Mφ did not significantly affect the proliferation of MEF that were treated with TGFβ1, however the CM-Mres inhibited significantly the TGFβ1 induced proliferation of MEFs cells (FIG. 13A). CM-AC during the first 48 hours had no significant effect on TGFβ1 induced MEFs proliferation, however at 72 hours it inhibited the proliferation significantly (p≤0.001) but still their proliferation was significantly (p≤0.001) higher compared to MEF treated with CM-Mres.

Figure 13B:
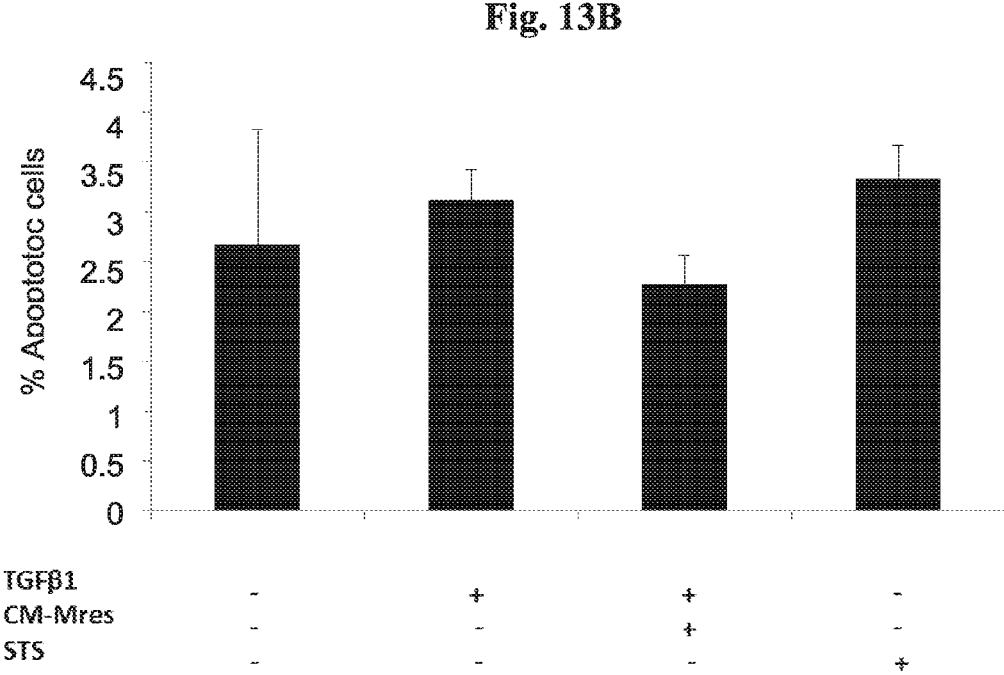

Next we explored whether the inhibition of MEF proliferation by the CM-Mres was due to cell cycle arrest or increase in apoptosis of MEF. Therefore, we tested apoptosis of the MEFs at 48 hours. At this time point significant changes in the proliferation of the cells was already observed as shown in FIG. 13A. Therefore, MEFs were either untreated or were induced to differentiate on 8 chamber glass slides and were pre-incubated with CM-Mres 1 hour prior to adding TGFβ1. As for positive control for apoptosis, MEFs were treated with staurosporine (STS; 1.5 µg/ml) for 4 hours. The cells were fixed and evaluated for apoptotic death by TUNEL staining. Our results demonstrate that low percentages of apoptotic cells were present in all treatments with no significant changes (FIG. 13B) including our positive control. Most of the MEFs (more than 96%) were alive and did not stain for TUNEL upon treatment with TGFβ1 and CM-Mres, indicating CM-Mres does not cause MEF cell death. However, it is noted that prolonged cell cycle arrest is expected to eventually induce apoptosis.

Example 12

CM-Mres Inhibit α-SMA expression by MEF Treated with TGFβ1

Figure 14A:
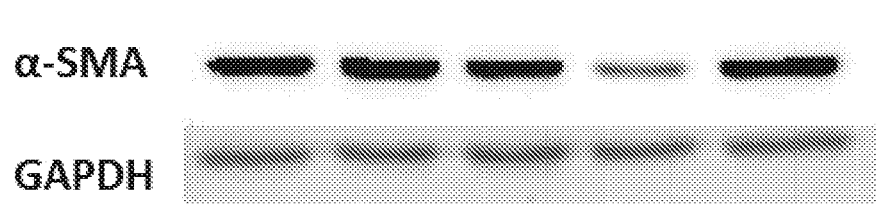
FIGS. 14A-14B show low expression of α-SMA in MEF cells treated with TGFβ1+ CM-Mres. A. Western blot analysis showing expression levels of α-SMA, representative blots from two independent experiments. B. Quantification of α-SMA expression levels by densitometry from two independent experiments. Values normalized to GAPDH (n=2; **: p≤0.01). From left to right: MEFs untreated, or treated with TGFβ1 alone or together with CM-Mφ, CM-Mres, or CM-AC.
Figure 14B:
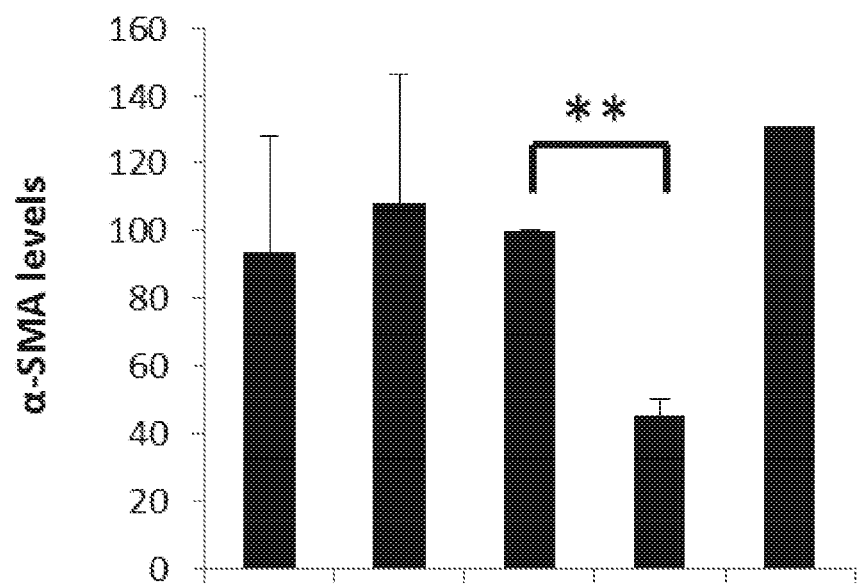

We further explored the effect of CM-Mres on differentiation of MEF to myofibroblasts by testing the expression of α-SMA. To this end, we either undifferentiated or differentiated MEF in the presence of CM-Mres, CM-Mφ, or CM-AC 1 hour before adding TGFβ1, for 72 hours. Protein lysates were collected and α-SMA levels were determined by western blot analysis. CM-Mres inhibited significantly the expression of α-SMA in MEF treated with TGFβ1 compared to the expression levels in MEF treated with TGFβ1+CM-Mφ (FIG. 14).

Example 13

CM-Mres Inhibit Type I Collagent Expression by MEF Treated with TGFβ1

Figure 15:
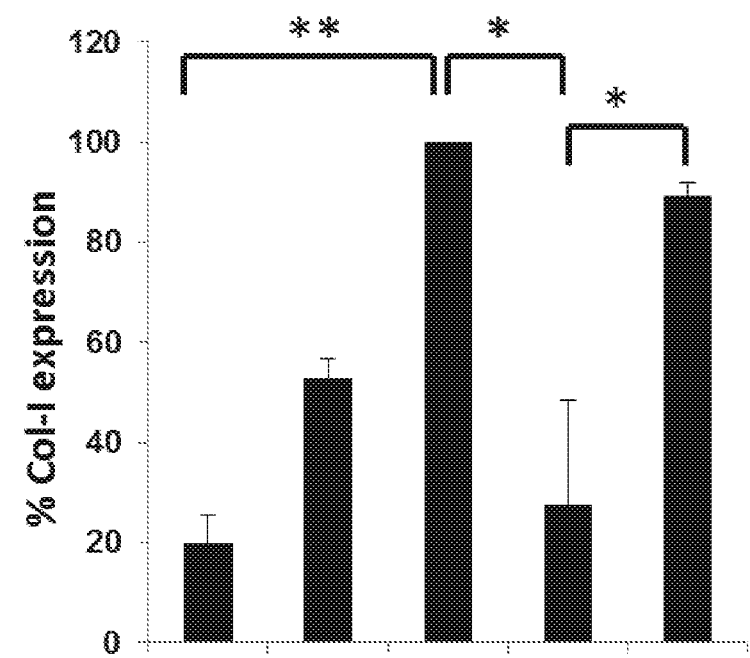
FIG. 15 shows that CM-Mres reduced the expression of type I collagen (Col-I) in TGFβ1-treated MEF. Percentage of Col-I expression is shown in MEFs treated from left to right: untreated, or treated with TGFβ1 alone or together with CM-Mφ, CM-Mres, or CM-AC. Values were normalized to TGFβ1-treated MEF with CM-Mφ (n=3; *: p≤0.05; **: p≤0.01).

Type I Collagen (Col-I) is expressed in differentiated fibroblasts. Therefore, we tested whether CM-Mres will inhibit Col-I expression in TGFβ1-treated MEF. To this end MEF were cultured on 8 chamber glass slides and were either untreated or treated with TGFβ1 in the presence of either CM-Mres, CM-Mφ or CM-AC. We determined Col-I expression by immunofluorescence staining and F-actin organization by phalloidin staining (data not shown). Our results demonstrated that CM-Mres significantly inhibited Col-I expression of TGFβ1 treated MEF compared to untreated MEF and to TGFβ1 treated MEF that were treated with either CM-Mφ or CM-AC (FIG. 15). Furthermore, a decrease in F-actin stress fibers was evident in MEF treated with TGFβ1+CM-Mres compared to MEF treated with TGFβ1 alone or in combination with either CM-Mφ or CM-AC (data not shown).

Example 14

CM-Mres Prevent Production of Col-I by Myofibroblast Cultured in 3D System

A novel 3D BME system to model tumor dormancy and outgrowth was described recently in Barkan et al., 2011. Furthermore, supplementing the 3D BME system with Col-I was shown previously to induce the transition of dormant D2.0R cells from quiescence to proliferative growth. Therefore, we wanted to explore whether MEF cultured in the 3D BME system will successfully differentiate to myofibroblasts, express Col-I and thus will induce dormant D2.0R cells outgrowth. If successful, we will test whether we can prevent the D2.0R cells outbreak by using CM-Mres. To this end MEF cells were cultured in the 3D BME system and were either untreated or treated with CM-Mφ, CM-AC or CM-Mres for 7days. Col-I expression was determined by immunofluorescence staining. Our results demonstrate that MEFs cultured in the 3D BME system differentiated to myofibroblasts given they expressed Col-I (FIG. 16). Furthermore, treatment with CM-Mres reduced significantly the expression of Col-I (FIG. 16). Hence, CM-Mres prevented the differentiation of MEF to myofibroblasts in the 3D BME system. Interestingly, as can also be seen from FIG. 16, cells treated either with CM-Mφ or with CM-AC showed increased Col-I expression, compared to untreated cells.

Example 15

Conditioned Media of Ex-Vivo Generated CD11b$^{low}$ Macrophages (CM-Mres) Inhibit Proliferation and Induce Cell Death of D2A1 Dormant Tumor Cells Peritoneal mouse macrophages were recovered 66 hours post peritonitis initiation and incubated either with no cells, or in the presence of apoptotic (AC) or live (LC) Jurkat cells. The unbound apoptotic cells were then washed and the macrophages were recovered and immunoassayed for CD11b expression on their surface. Expression of CD11b was determined by FACS analysis. As can be seen in FIG. 17A, incubation with apoptotic (AC) but not with live (LC) Jurkat cells, generated a macrophage population enriched with CD11b$^{low}$ cells (n32 5). Conditioned media from cells incubated with AC or LC were collected and assessed for their potential ability to directly affect the growth of dormant or out-breaking D2A1 cells by the 3D basement membrane (BME) system modeling tumor dormancy (Barkan et al., 2008).

The conditioned media were overlaid on D2A1 cells cultured in the 3D BME system on day 2 when cells are dormant, and on day 4, prior to their transition from quiescence to proliferation. Proliferation of the D2A1 cells was determined by using the Cell Titer 96 Aqueous One Solution cell proliferation assay kit (Protégé; Madison, Wis.) as described by Barkan et al. 2008.

Figure 17B:
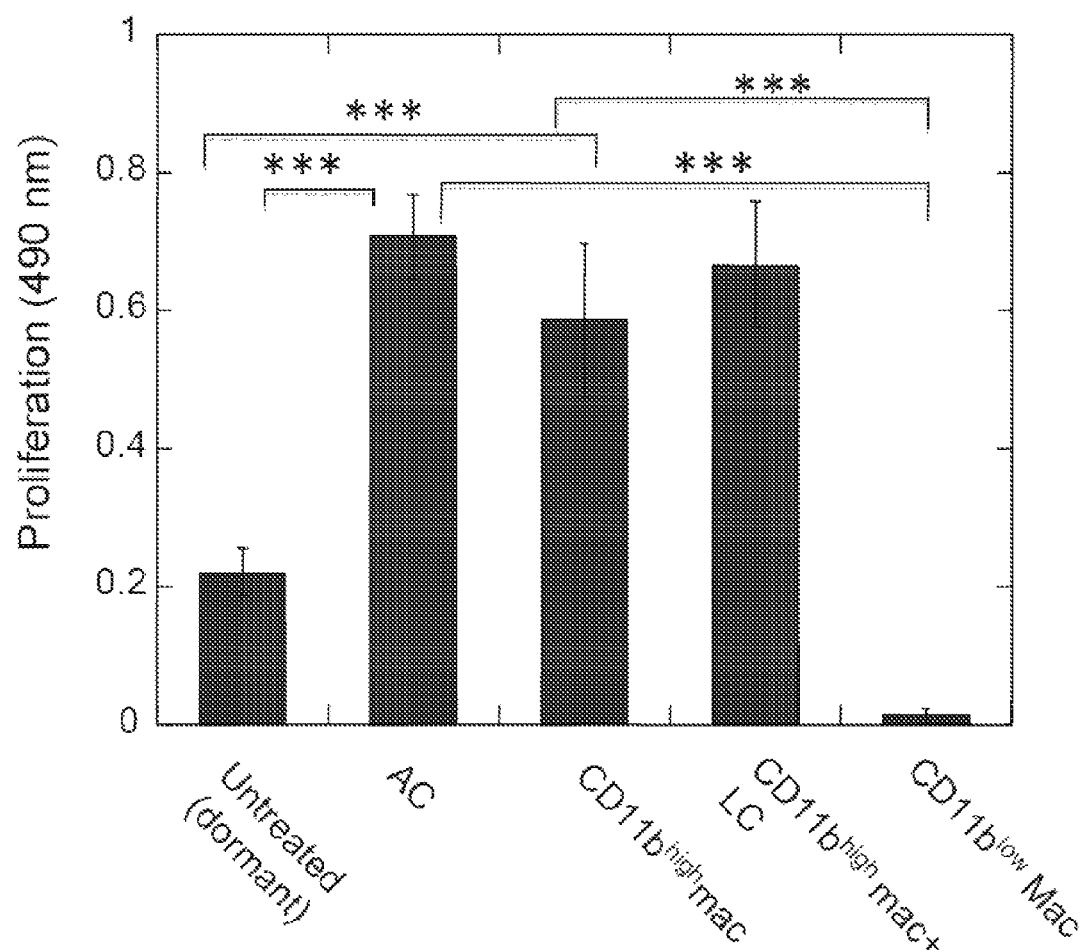

FIG. 17B shows proliferation of D2A1 cells in the 3D system overlaid on day 4for 96 h with either assay media for dormancy (DMEM low glucose (GIBCO), 2% fetal bovine serum (FBS), 1% penicillin-streptomycin and 2% BME (Trevigen Inc.)) (untreated), with RPMI incubated with apoptotic cells (AC), or with conditioned media obtained from macrophages incubated ex-vivo with RPMI+10% FBS+1% penicillin-streptomycin (CD11b$^{high}$mac), live (CD11b$^{high}$mac+LC), or apoptotic (CD11b$^{low}$mac) Jurkat cells. n=4; ***, P≤0.001.

The results demonstrate that conditioned media obtained from ex-vivo generated macrophages expressing low levels of CD11b (CD11b$^{low}$) induced cell death of outbreaking D2A1 cells during their transition from dormancy to proliferation in the 3D system.

Figure 17C:
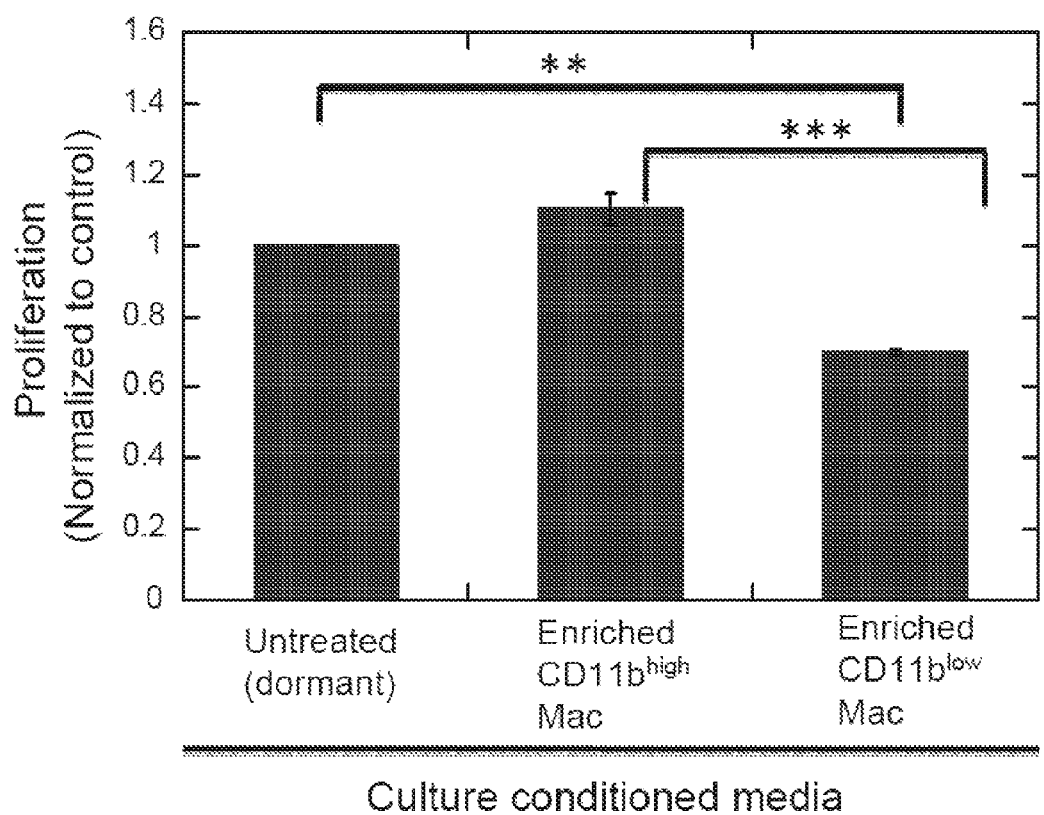

FIG. 17C shows proliferation of D2A1 cells in the 3D system overlaid on day 2 for 96 h with either DMEM low glucose (GIBCO), 2% fetal bovine serum (FBS), and 1% penicillin-streptomycin+2% BME (untreated), or with conditioned media obtained from cell preparations enriched for CD11b$^{high}$ or CD11b$^{low}$ macrophages as described above, supplemented also with 2% BME. Since the D2A1 cells are dormant at day 2, and remain dormant for 4-6 days, a measured reduction in proliferation indicates cell death of the cultured D2A1 cells.

The results indicate that soluble factors secreted by the CD11b$^{low}$ macrophages, which are present in the conditioned media, induce cell death of dormant D2A1 cells. Thus, dormant disseminated tumor cells may be eradicated by natural soluble factors produced by immune cells participating in physiological healing processes.

Example 16

CM-Mres Prevent Metastatic Outbreak of Dormant Tumor Cells Co-Cultured with Myofibroblasts Our findings demonstrated that culturing MEFs in the 3D BME system promoted their differentiation and the expression of Col-I and this differentiation was inhibited by treatment with CM-Mres. D2.0R cells cultured in the 3D BME system are dormant and supplementing the BME with Col-I was shown previously to induce their outbreak (Barkan et al., 2010a). Hence, based on our recent and previous results we next tested whether 1) co-culture of dormant D2.0R cells with MEF in the 3D BME system will induce their emergence from tumor dormancy to proliferative growth and 2) whether treatment with CM-Mres will inhibit Col-I expression and will prevent D2.0R cells outbreak. To this end we co-cultured D2.0R cells stably expressing green fluorescent protein (D2.0R-GFP) with MEF for 7 days. Our results showed that D2.0R-GFP cells cultured in the BME system remain dormant as expected, whereas co-culture of D2.0R-GFP cells with MEF in the 3D BME system, promoted their outbreak (dramatic increase in cell number) and Col-I expression was evident (data now shown). Similarly D2.0R-GFP cells emerged from their dormant state in the presence of MEF treated with CM-Mφ. However, treatment of the co-culture with CM-Mres prevented Col-I expression by the differentiated MEF and lower number of D2.0R-GFP were evident compared to untreated co-culture or co-culture treated with CM-Mφ.

Example 17

In Vivo Treatment of Dormant and Outbreaking Tumor Cells with CM-Mres

Conditioned media of ex-vivo generated CD11b$^{low}$ (CM-Mres) and control CD11b$^{high}$ macrophages (CM-Mφ) (as described in Example 9) is assayed for their impact on the metastatic outbreak in vivo, using tumor-inoculated mice. Experimental metastasis assay in athymic nude mice are carried out in female athymic nude mice (n=30) injected via tail vein with D2A1 cells stably expressing GFP (D2A1-GFP cells) to allow tracking by live video microscopy as described previously as described in Barkan et al. 2008 and 2010a. Prior to the outbreak of dormant D2A1-GFP cells (5 days post D2A1-GFP injection) 15 of the recipient mice are treated (50-100 μl, intranasal or via tail vain injection) with CM-Mφ. (control group), whereas the rest of the recipient mice (n32 15) are treated with CM-Mres (treated group). The control and treated groups are divided to 3 even groups (n=5; control groups A/B/C and treated groups A/B/C). Control and treated group B and C receive additional treatments at days 8 and 11 of either CM-Mφ or CM-Mres, respectively. Lungs from all groups (and untreated mice; n=5) are harvested 2 weeks post injection of D2A1-GFP cells, and tumor cells are analyzed for their dormant or metastatic growth using live video microscopy as described previously in Barkan et al. 2008 and 2010a. Imaged lungs are frozen in optimal cutting temperature (OCT) compound for determination of extent of fibrosis at the metastatic site by immunofluorescence staining for Col-I and macrophages (F4/80 staining) of frozen sections prepared from the harvested lungs.

Metastatic outbreak in the control groups treated with CM-Mφ, with possible enhancement of the extent of metastasis compared to untreated mice may be expected, whereas in the CM-Mres-treated group the number of lesions will decrease and the majority of the lesions are expected to be dormant with inhibition of a fibrotic stroma at the metastatic site (depicted by low expression of Col-I and clearance of macrophages).

The following experiments are repeated with highly metastatic human breast cancer cell line such as MDA-MB-231 cells. The mice are treated as above but at two weeks when metastatic lesions are already established.

In the CM-Mres-treated group, the number of lesions is expected to decrease and the majority of the lesions are expected to be dormant with inhibition of a fibrotic stroma at the metastatic site (depicted by low expression of Col-I and clearance of macrophages).

Example 18

Treatment of Tumor Metastasis by Administering Mres Macrophages

Ex-vivo generated peritoneal/lung pro-resolving CD11b$^{low}$ macrophages (Mres macrophages) are prepared as described in Example 9. Initially, a pilot experiment is conducted to determine the transfer regimen of the ex-vivo generated Mres macrophages required to promote inhibition of the metastatic outbreak in the lungs. The transfer is carried out by intranasal administration. To this end, experimental metastasis assays are carried out on recipient female athymic mice (n=30) that are injected via tail vein with D2A1-GFP cells in order to analyze later on their dormant and metastatic outbreak by live video microscopy as described previously in Barkan et al. 2008 and 2010a. Prior to the outbreak of dormant D2A1-GFP cells (5 days post D2A1-GFP injection), 15 of the recipient mice are transferred with isolated and sorted CD11b$^{high}$ macrophages obtained from 45 donor mice with peritonitis (control group), whereas the rest of the recipient mice (n=15 mice) are transferred with an equal number of sorted ex-vivo generated Mres macrophages (treated group). The control and treated groups are divided to 3 even groups: Control group A/B/C (n=5 mice per each group) and treated group A/B/C (n=5 mice per each group). Control and treated group B receive an additional transfer 3 days later of either freshly prepared pro-resolving CD11b$^{high}$ or ex-vivo generated Mres macrophages (as described above), respectively, whereas control and treated group C receive two additional transfers, at 3 day intervals, with either freshly prepared CD11b$^{high}$ or ex-vivo generated Mres macrophages, respectively. Lungs from all groups of mice are harvested 2 weeks post injection of D2A1-GFP cells, and tumor cells are analyzed for their dormant or metastatic growth using live video microscopy. Imaged lungs are frozen in OCT for determination of extent of fibrosis at the metastatic site by immunofluorescence staining for Col-I and macrophages (F4/80 staining) of frozen sections prepared from the harvested lungs.

Metastatic outbreak in the control group transferred with CD11b$^{high}$ macrophages is expected, with possible enhancement of the extent of metastasis, whereas in the treated group the majority of the lesions are expected to be dormant. Once the transfer regimen needed to inhibit the metastatic outbreak of D2A1-GFP cells is established, the experiment is repeated with a larger cohort of mice transferred with ex-vivo-generated peritoneal/lung Mres macrophages, and proceed to further confirm the promotion of resolution of the metastatic microenvironment as detailed below.

REFERENCES

Ariel A, Serhan C N: New Lives Given by Cell Death: Macrophage Differentiation Following Their Encounter with Apoptotic Leukocytes during the Resolution of Inflammation. *Frontiers in Immunology* 2012, 3:4.

Barkan D, Kleinman H, Simmons J L, Asmussen H, Kamaraju A K, Hoenorhoff M J, Liu Z Y, Costes S V, Cho E H, Lockett S et al: Inhibition of metastatic outgrowth from single dormant tumor cells by targeting the cytoskeleton. *Cancer Research* 2008, 68(15):6241-6250.

Barkan D, Green J E, Chambers A F: Extracellular matrix: a gatekeeper in the transition from dormancy to metastatic growth. *European Journal of Cancer* 2010, 46(7):1181-1188.

Barkan D, El Touny L H, Michalowski A M, Smith J A, Chu I, Davis A S, Webster J D, Hoover S, Simpson R M, Gauldie J et al: Metastatic growth from dormant cells induced by a col-I-enriched fibrotic environment. *Cancer Research* 2010a, 70(14):5706-5716.

Barkan D, Green J E: An in vitro system to study tumor dormancy and the switch to metastatic growth. *Journal of Visualized Experiments: JoVE* 2011(54).

Hasebe T, Sasaki S, Imoto S, Mukai K, Yokose T, Ochiai A: Prognostic significance of fibrotic focus in invasive ductal carcinoma of the breast: a prospective observational study. *Modern Pathology: an official journal of the United States and Canadian Academy of Pathology, Inc* 2002, 15(5):502-516.

Luo, Yi and Knudson, M. J., Mycobacterium bovis Bacillus Calmette-Guérin-Induced Macrophage Cytotoxicity against Bladder Cancer Cells, Clin Dev Immunol. 2010: 357591

Mantovani A. et al., 2004. The chemokines system in diverse forms of macrophage activation and polarization. *Trends Immunol*, 25, 677-86.

Mantovani A et al., 2005 Macrophage polarization comes of age. *Immunity*, 23, 344-.

Martinez et al., 2009. Alternative activation of macrophages: an immunologic functional perspective. *Annu Rev Immunol*, 27, 451-83.

Schif-Zuck S, Gross N, Assi S, Rostoker R, Serhan C N, Ariel A: Saturated-efferocytosis generates pro-resolving CD11b low macrophages: modulation by resolvins and glucocorticoids. *European Journal of Immunology* 2011, 41(2):366-379.

The invention claimed is:

1. A method for treating breast cancer, comprising administering to a subject in need an effective amount of an active agent selected from the group consisting of: (i) a conditioned cell culture medium of CD11b$^{low}$ macrophasges; and (ii) a pharmaceutical composition comprising (i) the conditioned cell culture medium of CD11b$^{low}$ macrophages, and a pharmaceutically active carrier, excipient or diluent, wherein said treatment of cancer comprises preventing or delaying cancer recurrence or occurrence of metastasis or inhibiting cancer metastasis.

2. The method according to claim 1, wherein said treating cancer, preventing or delaying cancer recurrence or occurrence of metastasis, or inhibiting cancer metastasis comprises preventing or inhibiting an outbreak of dormant cancer cells.

3. The method according to claim 1, wherein said subject in need is in cancer remission.

4. The method according to any of claims 1, wherein said dministering is performed in combination with additional one or more anti-cancer agents or treatments.

* * * * *

UNITED STATES PATENT AND TRADEMARK OFFICE
CERTIFICATE OF CORRECTION

PATENT NO. : 9,724,366 B2
APPLICATION NO. : 14/758569
DATED : August 8, 2017
INVENTOR(S) : Dalit Barkan It is certified that error appears in the above-identified patent and that said Letters Patent is hereby corrected as shown below:

On the Title Page

Item (71), (Applicant) at Line 1, Change "UNIVRSITY" to --UNIVERSITY--.

In Column 2 item (56) at Line 32, Under Other Publications, change "in flammation" to --inflammation--.

In the Drawings

Sheet 11 of 27 (Fig. 7C) at Line 2 (Y-axis), Change "macrophagues" to --macrophages--.

Sheet 11 of 27 (Fig. 7C) at Line 3 (Y-axis), Change "macrophagues)" to --macrophages)--.

In the Specification

In Column 2 at Line 47, Change "TGFP" to --TGFβ--.

In Column 4 at Line 52, Change "and or" to --and/or--.

In Column 6 at Line 55, Change "glucorticoid" to --glucocorticoid--.

In Column 7 at Line 26, Change "a a" to --a--.

In Column 10 at Line 63, Change "(CM-Mck)." to --(CM-Mφ).--.

In Column 13 at Line 59, Change "TGFP," in --TGFβ,--.

In Column 14 at Line 10, Change "CD11b$^{high}$" to --CD11b$^{low}$--.

In Column 14 at Line 19, Change "CD11b$^{high}$" to --CD11b$^{low}$--.

Signed and Sealed this
Tenth Day of April, 2018

Andrei Iancu
*Director of the United States Patent and Trademark Office*

CERTIFICATE OF CORRECTION (continued)
U.S. Pat. No. 9,724,366 B2

In Column 15 at Line 56, Change "TGFP, PPARX" to --TGFβ, PPARλ--.

In Column 15 at Line 65, Change "(0.5 ρM)," to --(0.5 μM),--.

In Column 16 at Line 9, Change "glucorticoid." to --glucocorticoid.--.

In Column 16 at Line 14 (approx.), Change "RvE 1," to --RvE1,--.

In Column 17 at Line 20, Change "parentersl" to --parenteral--.

In Column 18 at Line 9, Change "condition," to --condition.--.

In Column 19 at Line 35, Change "Lapatinib." to --Lapatinib).--.

In Column 19 at Line 44 (approx.), Change "Decarbazine," to --Dacarbazine,--.

In Column 19 at Line 45 (approx.), Change "Methotraxate," to --Methotrexate,--.

In Column 21 at Line 6, Change "ere" to --were--.

In Column 21 at Lines 33-34, Change "intraperitonealy" to --intraperitoneally--.

In Column 24 at Line 63, Change "2Images" to --2D Images--.

In Column 25 at Line 59, Change "F4/80was" to --F4/80 was--.

In Column 26 at Line 44 (approx.), Change "CD11b$^{high}$" to --CD11b$^{low}$--.

In Column 28 at Line 21, Change "TGFP," to --TGFβ,--.

In Column 30 at Line 11, Change "(CM-Mck)" to --(CM-Mφ)--.

In Column 32 at Line 11 (approx.), Change "Collagent" to --Collagen--.

In Column 33 at Line 8, Change "(n32 5)." to --(n=5).--.

In Column 33 at Line 22, Change "4for" to --4 for--.

In Column 34 at Line 36 (approx.), Change "(n32 15)" to --(n=15)--.

In Column 36 at Line 26, After "357591" insert --.--.

In the Claims

In Column 36 at Line 44, In Claim 1, change "macrophasges;" to --macrophages;--.

CERTIFICATE OF CORRECTION (continued)
U.S. Pat. No. 9,724,366 B2

In Column 36 at Line 58, In Claim 4, before "claims" delete "any of".

In Column 36 at Line 59, In Claim 4, change "dministering" to --administering--.